(12) United States Patent
Jung et al.

(10) Patent No.: US 10,575,785 B2
(45) Date of Patent: Mar. 3, 2020

(54) METHOD AND APPARATUS FOR OBTAINING BIOMETRIC INFORMATION

(71) Applicant: Samsung Electronics Co., Ltd., Gyeonggi-do (KR)

(72) Inventors: Sun Ok Jung, Gyeonggi-do (KR); Dong Wook Kim, Seoul (KR); See Youn Kwon, Seoul (KR)

(73) Assignee: Samsung Electronics Co., Ltd., Yeongtong-gu, Suwon-si, Gyeonggi-do (KR)

( * ) Notice: Subject to any disclaimer, the term of this patent is extended or adjusted under 35 U.S.C. 154(b) by 491 days.

(21) Appl. No.: 14/996,598

(22) Filed: Jan. 15, 2016

(65) Prior Publication Data

US 2016/0228064 A1 Aug. 11, 2016

(30) Foreign Application Priority Data

Feb. 5, 2015 (KR) ........................ 10-2015-0018193

(51) Int. Cl.
*A61B 5/04* (2006.01)
*A61B 5/00* (2006.01)
*G06F 1/16* (2006.01)
*A61B 5/024* (2006.01)
*A61B 5/0404* (2006.01)
*A61B 5/145* (2006.01)
*G06K 9/00* (2006.01)
*H04N 5/225* (2006.01)

(52) U.S. Cl.
CPC .......... *A61B 5/6898* (2013.01); *A61B 5/0022* (2013.01); *A61B 5/02438* (2013.01); *A61B 5/0404* (2013.01); *A61B 5/14542* (2013.01); *A61B 5/4872* (2013.01); *A61B 5/74* (2013.01); *G06F 1/1656* (2013.01); *G06F 1/1684* (2013.01); *G06F 1/1686* (2013.01); *G06K 9/00885* (2013.01); *H04N 5/225* (2013.01); *A61B 2562/04* (2013.01); *G06K 2009/00939* (2013.01)

(58) Field of Classification Search
CPC ... A61B 5/0402; A61B 5/0006; A61B 5/0205; A61B 5/04085; A61B 5/0537
USPC .................. 600/372, 382–393, 508–509, 301
See application file for complete search history.

(56) References Cited

U.S. PATENT DOCUMENTS

| 4,375,219 A * | 3/1983 | Schmid .............. A61B 5/02438 |
| | | 600/393 |
| 7,647,093 B2 * | 1/2010 | Bojovic .............. A61B 5/0006 |
| | | 600/509 |
| 8,615,290 B2 | 12/2013 | Lin et al. |

(Continued)

FOREIGN PATENT DOCUMENTS

| CN | 1706145 A2 | 12/2005 |
| JP | 2006-26209 A | 2/2006 |
| KR | 10-2005-0103355 A | 10/2005 |

OTHER PUBLICATIONS

European Search Report dated Jul. 11, 2016.
Chinese Search Report dated Oct. 25, 2019.

*Primary Examiner* — Joseph A Stoklosa
*Assistant Examiner* — Brian M Antiskay
(74) *Attorney, Agent, or Firm* — Cha + Reiter, LLC.

(57) ABSTRACT

An electronic device comprising: a housing; a first structure extending outwardly from a surface of the housing; and a plurality of first electrodes disposed on the first structure and separated from each other by an insulating material.

12 Claims, 10 Drawing Sheets

(56) References Cited

U.S. PATENT DOCUMENTS

| | | | |
|---|---|---|---|
| 8,897,868 B2* | 11/2014 | Mazar | A61B 5/0402 600/386 |
| 9,770,185 B2* | 9/2017 | Wheeler | A61B 5/0533 |
| 10,313,501 B2 | 6/2019 | Bloomberg et al. | |
| 2003/0101348 A1 | 5/2003 | Russo et al. | |
| 2003/0115475 A1 | 6/2003 | Russo et al. | |
| 2003/0115490 A1 | 6/2003 | Russo et al. | |
| 2003/0126448 A1 | 7/2003 | Russo | |
| 2003/0157904 A1 | 8/2003 | Bloomberg et al. | |
| 2005/0027203 A1* | 2/2005 | Umeda | A61B 5/0404 600/509 |
| 2007/0021677 A1* | 1/2007 | Markel | A61B 5/0006 600/509 |
| 2007/0274575 A1 | 11/2007 | Russo | |
| 2007/0299322 A1* | 12/2007 | Miyajima | A61B 5/0008 600/301 |
| 2010/0113950 A1 | 5/2010 | Lin et al. | |
| 2011/0015496 A1* | 1/2011 | Sherman | A61B 5/0006 600/301 |
| 2011/0301435 A1* | 12/2011 | Albert | A61B 5/0404 600/301 |
| 2011/0306859 A1* | 12/2011 | Saldivar | A61B 5/6823 600/365 |
| 2012/0022385 A1* | 1/2012 | Shimuta | A61B 5/0404 600/509 |
| 2012/0116176 A1* | 5/2012 | Moravec | A61B 5/6898 600/300 |
| 2012/0116240 A1* | 5/2012 | Chou | A61B 5/0404 600/523 |
| 2013/0172723 A1* | 7/2013 | Baxi | A61B 5/04085 600/384 |
| 2014/0051941 A1 | 2/2014 | Messerschmidt | |
| 2014/0114166 A1* | 4/2014 | Baxi | A61B 5/0404 600/384 |
| 2014/0171776 A1 | 6/2014 | Lin et al. | |
| 2014/0176335 A1 | 6/2014 | Brumback et al. | |
| 2014/0176346 A1 | 6/2014 | Brumback et al. | |
| 2014/0176422 A1 | 6/2014 | Brumback et al. | |
| 2014/0180595 A1 | 6/2014 | Brumback et al. | |
| 2014/0249438 A1 | 9/2014 | Morikawa et al. | |
| 2014/0276153 A1* | 9/2014 | Amitai | A61B 5/04028 600/509 |
| 2014/0317722 A1 | 10/2014 | Tartz et al. | |
| 2014/0334083 A1 | 11/2014 | Bailey | |
| 2015/0018660 A1* | 1/2015 | Thomson | A61B 5/0404 600/393 |
| 2015/0073285 A1* | 3/2015 | Albert | A61B 5/0408 600/509 |
| 2016/0038055 A1* | 2/2016 | Wheeler | A61B 5/0533 600/547 |
| 2016/0081572 A1* | 3/2016 | Hong | A61B 5/6898 600/301 |
| 2016/0157749 A1* | 6/2016 | Bohorquez | A61B 5/0537 600/393 |

\* cited by examiner

METHOD AND APPARATUS FOR OBTAINING BIOMETRIC INFORMATION

CLAIM OF PRIORITY

This application claims the benefit under 35 U.S.C. § 119(a) of a Korean patent application filed on Feb. 5, 2015 in the Korean Intellectual Property Office and assigned Serial number 10-2015-0018193, the entire disclosure of which is hereby incorporated by reference.

TECHNICAL FIELD

The present disclosure relates to electronic devices, in general, and more particularly to a method and apparatus for obtaining biometric information.

BACKGROUND

An electronic device, e.g., a smartphone, performs a variety of functions, e.g., a communication function, a camera function, an image reproducing function, etc. In recent years, demands for healthcare applications or personal health-measuring devices keep increasing since interest in health is increasing, and thus electronic devices with various functions to support healthcare and health-managing have been developed. In addition, as the market demand for mobile medical devices that measure health status anywhere and at any time continues to increases, an electronic device, such as a smartphone on which a biometric sensor checking the health status of a user is mount, has been released.

However, in a conventional electronic device, an electrode performing the above-mentioned functions is disposed in a separated area different from an area in which a module performing different functions from the above-mentioned functions is disposed. For instance, in a few smartphone models, a heart rate sensor (e.g., an electrode) for measuring a heart rate is placed in a separate area different from other modules mounted on a rear side of the electronic device. In this case, the area in which the electrode is placed is used to only measure biometric information. In addition, when considering the areas in which modules (e.g., a camera, a flash, a button, etc.) supporting different functions included in the electronic device, the area for the arrangement of the electrode causes problems with space utilization and visual appearance issues.

SUMMARY

According to aspects of the disclosure, an electronic device is provided comprising: a housing; a first structure extending outwardly from a surface of the housing; and a plurality of first electrodes disposed on the first structure and separated from each other by an insulating material.

According to aspects of the disclosure, a method is provided for use in an electronic device having a housing and a first structure disposed on the housing, the method comprising: obtaining biometric information of a user by using a plurality of first electrodes disposed on the first structure and separated from each other by an insulating material; and identifying a health status of the user based on the biometric information.

According to aspects of the disclosure, a non-transitory computer readable medium is provided storing one or more processor-executable instructions, which when executed by at least one processor cause the at least one processor to execute a process comprising the steps of: obtaining biometric information of a user by using a plurality of first electrodes disposed on a first structure that is arranged on a housing of an electronic device, the plurality of first electrodes being separated from each other by an insulating material; and identifying a health status of the user based on the biometric information.

BRIEF DESCRIPTION OF THE DRAWINGS

The above and other aspects, features, and advantages of certain embodiments of the present disclosure will be more apparent from the following description taken in conjunction with the accompanying drawings, in which.

Throughout the drawings, it should be noted that like reference numbers are used to depict the same or similar elements, features, and structures.

DETAILED DESCRIPTION

Figures 1A, 1B:
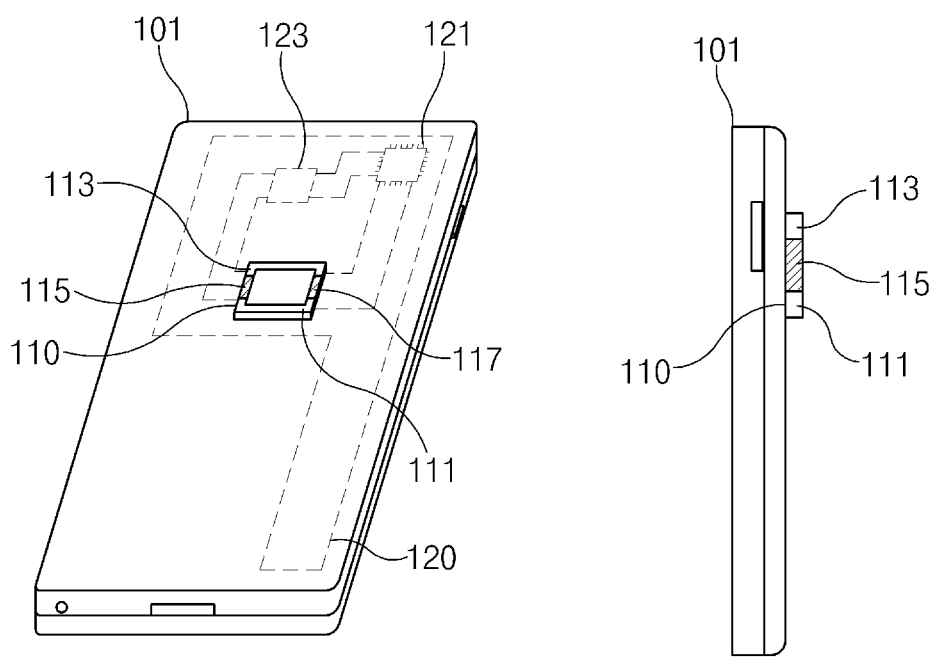
FIG. 1A illustrates a perspective view of an example of an electronic device, according to various embodiments of the present disclosure.
FIG. 1B illustrates a side view of the electronic device of FIG. 1A, according to various embodiments of the present disclosure.

Various embodiments of the present disclosure may be described with reference to accompanying drawings. Accordingly, those of ordinary skill in the art will recognize that modification, equivalent, and/or alternative on the various embodiments described herein can be variously made without departing from the scope and spirit of the present disclosure. With regard to description of drawings, similar components may be marked by similar reference numerals.

In the disclosure disclosed herein, the expressions "have", "may have", "include" and "comprise", or "may include" and "may comprise" used herein indicate existence of corresponding features (e.g., elements such as numeric values, functions, operations, or components) but do not exclude presence of additional features.

In the disclosure disclosed herein, the expressions "A or B", "at least one of A or/and B", or "one or more of A or/and B", and the like used herein may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used herein may refer to various elements of various embodiments of the present disclosure, but do not limit the elements. For example, such terms do not limit the order and/or priority of the elements. Furthermore, such terms may be used to distinguish one element from another element. For example, "a first user device" and "a second user device" indicate different user devices. For example, without departing the scope of the present disclosure, a first element may be referred to as a second element, and similarly, a second element may be referred to as a first element.

It will be understood that when an element (e.g., a first element) is referred to as being "(operatively or communicatively) coupled with/to" or "connected to" another element (e.g., a second element), it can be directly coupled with/to or connected to the other element or an intervening element (e.g., a third element) may be present. In contrast, when an element (e.g., a first element) is referred to as being "directly coupled with/to" or "directly connected to" another element (e.g., a second element), it should be understood that there are no intervening elements (e.g., a third element).

According to the situation, the expression "configured to" used herein may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other components. For example, a "processor configured to perform A, B, and C" may mean a dedicated processor (e.g., an embedded processor) for performing a corresponding operation or a generic-purpose processor (e.g., a central processing unit (CPU) or an application processor) which may perform corresponding operations by executing one or more software programs which are stored in a memory device.

Terms used in this specification are used to describe specified embodiments of the present disclosure and are not intended to limit the scope of the present disclosure. The terms of a singular form may include plural forms unless otherwise specified. Unless otherwise defined herein, all the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal detect unless expressly so defined herein in various embodiments of the present disclosure. In some cases, even if terms are terms which are defined in the specification, they may not be interpreted to exclude embodiments of the present disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, wearable devices (e.g., head-mounted-devices (HMDs), such as electronic glasses), an electronic apparel, electronic bracelets, electronic necklaces, electronic appcessories, electronic tattoos, smart mirrors, smart bands, smart watches, and the like.

According to various embodiments of the present disclosure, the electronic devices may be smart home appliances. The smart home appliances may include at least one of, for example, televisions (TVs), digital versatile disc (DVD) players, audios, refrigerators, air conditioners, cleaners, ovens, microwave ovens, washing machines, air cleaners, set-top boxes, TV boxes (e.g., Samsung HomeSync™, Apple TV™, or Google TV™), game consoles (e.g., Xbox™ and PlayStation™), electronic dictionaries, electronic keys, camcorders, electronic picture frames, and the like.

According to various embodiments of the present disclosure, the electronic devices may include at least one of medical devices (e.g., various portable medical measurement devices (e.g., a blood glucose monitoring device, a heartbeat measuring device, a blood pressure measuring device, a body temperature measuring device, and the like)), a magnetic resonance angiography (MRA), a magnetic resonance imaging (MRI), a computed tomography (CT), scanners, and ultrasonic devices) receiving a user input in an idle mode, navigation devices, global positioning system (GPS) receivers, event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller's machines (ATMs), points of sales (POSs), or internet of things (e.g., light bulbs, various sensors, electric or gas meters, sprinkler devices, fire alarms, thermostats, street lamps, toasters, exercise equipment, hot water tanks, heaters, boilers, and the like).

According to a certain embodiment of the present disclosure, the electronic devices may include at least one of furniture or buildings/structures, electronic boards, electronic signature receiving devices, projectors, or various measuring instruments (e.g., water meters, electricity meters, gas meters, or wave meters, and the like). The electronic devices according to an embodiment of the present disclosure may be one or more combinations of the above-mentioned devices. According to a certain embodiment of the present disclosure, an electronic device may be a flexible electronic. Also, electronic devices according to various embodiments of the present disclosure are not limited to the above-mentioned devices, and may include new electronic devices according to technology development.

Hereinafter, electronic devices according to an embodiment of the present disclosure will be described with reference to the accompanying drawings. The term "user" used herein may refer to a person who uses an electronic device or may refer to a device (e.g., an artificial electronic device) that uses an electronic device.

FIG. 1A illustrates a perspective view of an example of an electronic device, according to various embodiments of the present disclosure.

Referring to FIG. 1A, the electronic device 101 may include a housing forming an external enclosure of the electronic device 101, one or more structures 110 disposed on at least one surface of the housing, and a printed circuit board 120 disposed inside the housing. The housing may include a front surface, a rear surface opposite to the front surface, and a side surface surrounding the space between the front surface and the rear surface.

The structure 110 may be disposed on one surface (e.g., the front surface, the rear surface, or the side surface) of the housing. In some implementations, the structure 110 may protrude outwardly from the surface of the housing. Alternatively, the structure 110 may be recessed into the surface of the housing, or be flush with the surface of the housing. The structure 110 may include any suitable type of component of the electronic device. For example, the structure 110 may include module performing various functions (e.g., a photographing function, a biometric information measuring function, an input function, etc.) included in the electronic device 101 or a hardware device. In some implementations, the structure 110 may include one or more of a camera, a biometric sensor, or a button (e.g., a home button).

According to various embodiments, the structure 110 may include a first electrode 111, a second electrode 113, a first insulator 115, and a second insulator 117. According to an embodiment, the first electrode 111, the second electrode 113, the first insulator 115, and the second insulator 117 may be disposed on the surface of the structure 110, e.g., at the edge of the structure 110. According to various embodiments, the first electrode 111 and the second electrode 113 may be a conductor forming the edge of the structure 110. In addition, the first insulator 115 and the second insulator 117 may include an insulating material and may be disposed in a predetermined area of the structure 110 to divide the electrode (e.g., the first electrode 111 or the second electrode 113) or to separate electrodes from each other in order to prevent them from making contact. Referring to FIG. 1A, the first and second insulators 115 and 117 of the structure 110 may be disposed between the first and second electrodes 111 and 113 to prevent the first and second electrodes 111 and 113 from coming into contact with each other. According to various embodiments, the electronic device 101 may further include at least one additional structure that is different from the structure 110 and at least one electrode may be disposed in a predetermined area of the additional structure. For instance, the electrode may be disposed on the surface and/or edge of the additional structure. The additional structure may include any suitable type of component of the electronic device 101 (e.g., a home button) and it may be disposed on a front surface or a side surface of the electronic device 101.

According to various embodiments, the first electrode 111 or the second electrode 113 may be a biometric electrode that makes contact with a portion of a user' body to measure the biometric information (e.g., biometric resistance information, biometric electric potential information, etc.). According to an embodiment, the first electrode 111 or the second electrode 113 may be a measuring electrode or a ground electrode, which is related to the measurement of the biometric information. In some implementations, electrodes spaced apart from each other by a predetermined distance may be utilized as the biometric electrode (e.g., the measuring electrode or the ground electrode). In such instances, the biometric information obtained via the biometric electrode may be provided to at least one of a processor 121 and/or a biometric information processing module 123.

The printed circuit board 120 may be disposed inside the housing and electrically connected to any of the electrodes disposed on the structure 110. In addition, the printed circuit board 120 may include at least one module arranged to perform a specific function or may be electrically connected to one such module. The function may include any suitable type of function, such as a control function, a calculation function, a communication function, or a storage function.

According to various embodiments, the printed circuit board 120 may be connected to the processor 121. The processor 121 may perform a calculating or data processing operation about control and/or communication of elements related to the biometric information measurement. For instance, the processor 121 may analyze, store, or output the biometric information obtained via the electrodes (e.g., the first electrode 111 or the second electrode 113). According to an embodiment, the processor 121 may generate health status information for the user based on the biometric information. Afterwards, the processor 121 may store the health status information in memory, output the health status information via an output device, and/or transmit the health status information to an external device. More particularly, according to various embodiments, the processor 121 may control to store at least one of the biometric information or the health status information in a memory included in the electronic device 101. Additionally or alternatively, the processor 121 may store at least one of the biometric information or the health status information in an external device connected to the electronic device 101 by a network system. Additionally or alternatively, according to various embodiments, the processor 121 may output at least one of the biometric information and/or health status information on a display of the electronic device and/or a speaker of the electronic device. Additionally or alternatively, the electronic device may transmit at least some of the biometric information and/or health status to another device that is connected to the electronic device via a communications network.

In some implementations, the printed circuit board 120 may include the biometric information processing module 123 or may be connected to the biometric information processing module 123. The biometric information processing module 123 may perform a process of amplifying or converting the biometric information. The biometric information processing module 123 may then provide the amplified or converted biometric information to the processor 121. The biometric information processing module 123 may amplify the biometric information provided through the electrodes, remove noise included in the biometric information, or convert the biometric information, and then may supply the biometric information to the processor 121. For instance, the biometric information may include biometric electric potential information obtained through electrodes associated with an electrocardiogram (ECG) sensor. According to various embodiments, the biometric information processing module 123 may be integrated into the processor 121 or may be implemented separately from the processor 121.

FIG. 1B illustrates a perspective view of the electronic device of FIG. 1A, according to various embodiments of the present disclosure. FIG. 1B shows the structure 110 disposed on the rear surface of the electronic device 101 to be protruded outward from the rear surface of the electronic device 101. As described above, the first and second electrodes 111 and 113 may not be directly connected to each other by the first insulator 115 and the second insulator (not shown) and may be disposed in the predetermined area of the edge of the structure 110. Hereinafter, one or more electrodes and processors, which are disposed using specific areas of various structures will be described with reference to embodiments described below.

Figure 2:
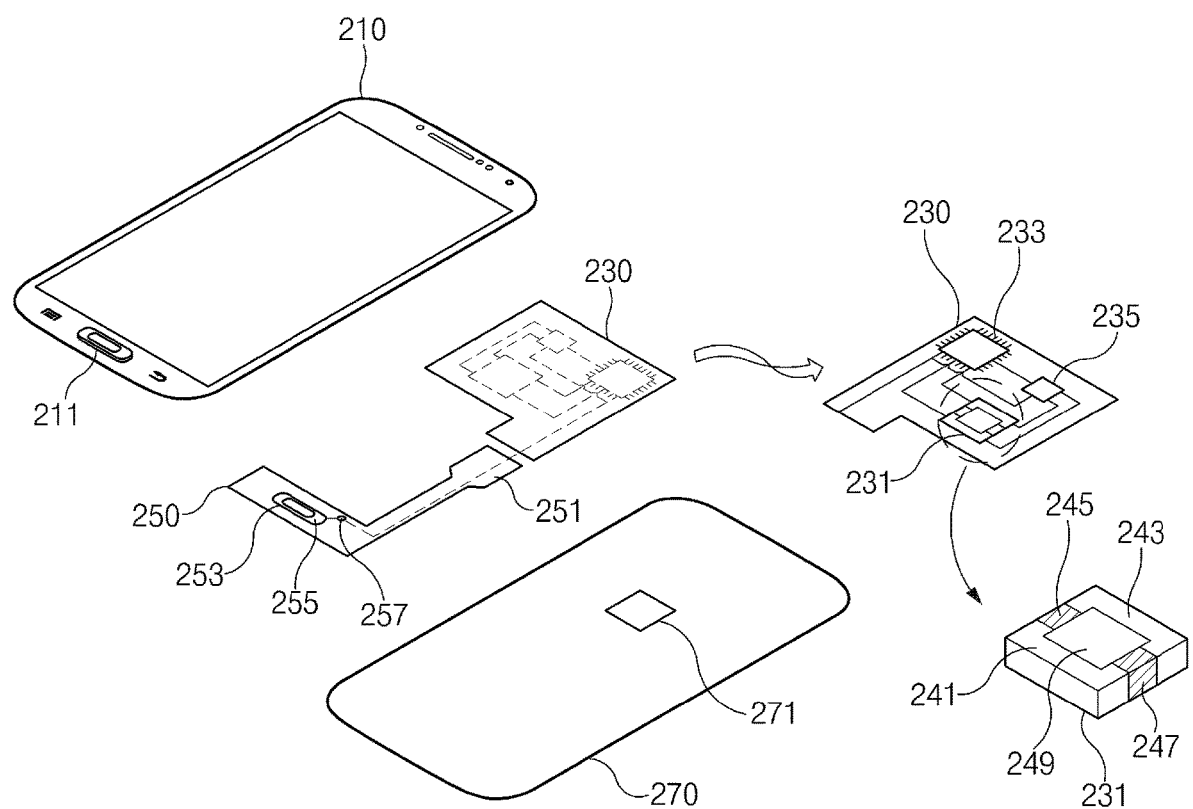
FIG. 2 illustrates an exploded perspective view of an example of an electronic device, according to various embodiments of the present disclosure.

FIG. 2 illustrates an exploded perspective view of an example of an electronic device, according to various embodiments of the present disclosure.

As illustrated, the electronic device may include the physical button 211 (e.g., a home button) disposed on a front surface 210 thereof. According to an embodiment, the physical button 211 may include an electrode disposed in a specific area thereof. For instance, one electrode may be disposed on the edge and/or a surface of the physical button 211. According to another embodiment, the physical button 211 may include a plurality of electrodes disposed on the edge thereof and a plurality of insulators disposed between the electrodes such that the electrodes are not directly connected to each other.

According to various embodiments, the electronic device (e.g., the electronic device 101) may include a first printed circuit board 230 and a second printed circuit board 250. According to an embodiment, the first printed circuit board 230 and the second printed circuit board 250 may be integrated together. Additionally or alternatively, the first and second printed boards may be separate from each other, and connected via a printed circuit board connector 251.

The first printed circuit board 230 may be connected to a biometric sensor 231 and a processor 233. In addition, the first printed circuit board 230 may further include a biometric information processing module 235. The biometric sensor 231 may be a module performing a function of measuring the biometric information as an example of the structure 110 shown in FIG. 1A and FIG. 1B. Although in the present example the biometric information module 235 is integrated into the printed circuit board 230, in some implementations the biometric module 235 may be implemented on a separate printed circuit board that is connected to the printed circuit board 230.

The biometric sensor 231 may include any suitable type of sensor, such as a photoplethysmogram (PPG) sensor. In this case, the biometric sensor 231 may include a first electrode 241, a second electrode 243, a first insulator 245, a second insulator 247, and a PPG sensor measuring part 249. According to an embodiment, the first electrode 241, the second electrode 243, the first insulator 245, and the second insulator 247 may be disposed on the edge of the biometric sensor 231. In addition, the PPG sensor measuring part 249 may be disposed in a specific area in the interior of the biometric sensor 231. The PPG sensor measuring part 249 may include light emitting diodes (LEDs) emitting a light having a predetermined specific wavelength and a photodiode measuring the light transmitting through the user's body or reflected by the user's body after being emitted from the LEDs. In this regard, the PPG sensor may measure a concentration of hemoglobin having different light absorbances from each other in accordance with a frequency of the light using a noninvasive method to measure the heart rate or an oxygen saturation level.

The processor 233 (e.g., the process 121) may analyze, store, or output the biometric information obtained by the biometric sensor 231 via at least one of the electrodes (e.g., the first electrode 241 and the second electrode 243) disposed on the edge of the biometric sensor 231. According to an embodiment, the processor 233 may analyze the biometric information obtained by the biometric sensor 231 and the electrodes. More specifically, the processor 233 may obtain the biometric information through the biometric sensor 231 and the electrodes, and then generate the health status information including more various information in comparison to the health status information when the processor 233 obtains the biometric information by only using the biometric sensor 231 or the biometric information by only using the electrodes.

The biometric information processing module 235 (e.g., the biometric information processing module 123) may amplify or convert the biometric information. The biometric information processing module 235 may amplify or convert the biometric information obtained through the electrodes or the biometric sensor 231 and provide the amplified or converted biometric information to the processor 233. According to an embodiment, the biometric information processing module 235 may be included in the biometric sensor 231 or the processor 233 or it may be implemented independently from the biometric sensor 231 or the processor 233.

The second printed circuit board 250 may include a circuit, component, or hardware device arranged to perform a function when the physical button 211 is pressed. The physical button 211 may be disposed in a specific area (e.g., a front lower area) of the electronic device or may be connected to the circuit, component, or hardware device. The second printed circuit board 250 may include the printed circuit board connector 251, a button connection area 253, a third electrode 255, and a hole 257. The button connection area 253 may electrically or physically connect the physical button 211 disposed at the front surface of the electronic device and the second printed circuit board 250. According to an embodiment, the button connection area 253 may include a touch sensor to determine an activation of the physical button 211 when the physical button 211 is pressed with a force that exceeds a predetermined level and/or when a variation in current occurs due to contact with the body of a user. In addition, the button connection area 253 may include the third electrode 255 for measuring biometric information. For example, the third electrode 255 may be formed on the edge of the physical button 211 disposed on the front surface of the electronic device and may be included in the second printed circuit board 250. As another example, the third electrode 255 may constitute a specific area of the edge or the surface of the physical button 211 and may be electrically or physically connected to the button connection area 254 included in the second printed circuit board 250. According to various embodiments, the third electrode 255 may begin supplying biometric information to the processor and/or biometric information processing module when the touch sensor included in the button connection area 254 comes in contact of the user's body. The hole 257 may serve as a connection path for a line connecting the third electrode 255 and at least one of the processor 233 or the biometric information processing module 235, which is disposed on the first printed circuit board 230.

According to various embodiments, the electronic device (e.g., the electronic device 101) may include a battery cover 270. The battery cover 270 may constitute one side surface of the housing. For instance, the battery cover 270 may be provided in a shape attachable to and detachable from the rear surface of the housing to cover a battery attached to or detached from the electronic device. The battery cover 270 may include an opening 271 formed therethrough such that the biometric sensor 231 disposed on the first printed circuit board 230 protrudes through the opening. According to various embodiments, the biometric sensor 231 may be coupled to a rear cover (not shown) of the electronic device, which is disposed between the printed circuit board and the battery cover 270. In such instances, the first printed circuit board 230 may include a separate connection area (not shown) or a connector (not shown) to be connected to the biometric sensor 231.

As described above, the electrodes, which are disposed on the physical button 211 and the biometric sensor 231, and the processor 233 may be used to measure various types of biometric information. According to an embodiment, the electronic device (e.g., the electronic device 101) may measure an electrocardiogram or a body fat ratio of a user through the first and second electrodes 241 and 243 disposed on the biometric sensor 231 (e.g., the PPG sensor) and the third electrode 255 disposed on the physical button 211. In addition, the electronic device may measure the heart rate and/or the oxygen saturation level of the user through the biometric sensor 231. Based on these measurements, the electronic device may obtain health status information of the user that indicates and/or identifies one or more of heart disease, stress, fatigability, vascular age, blood pressure, etc.

Figure 3:
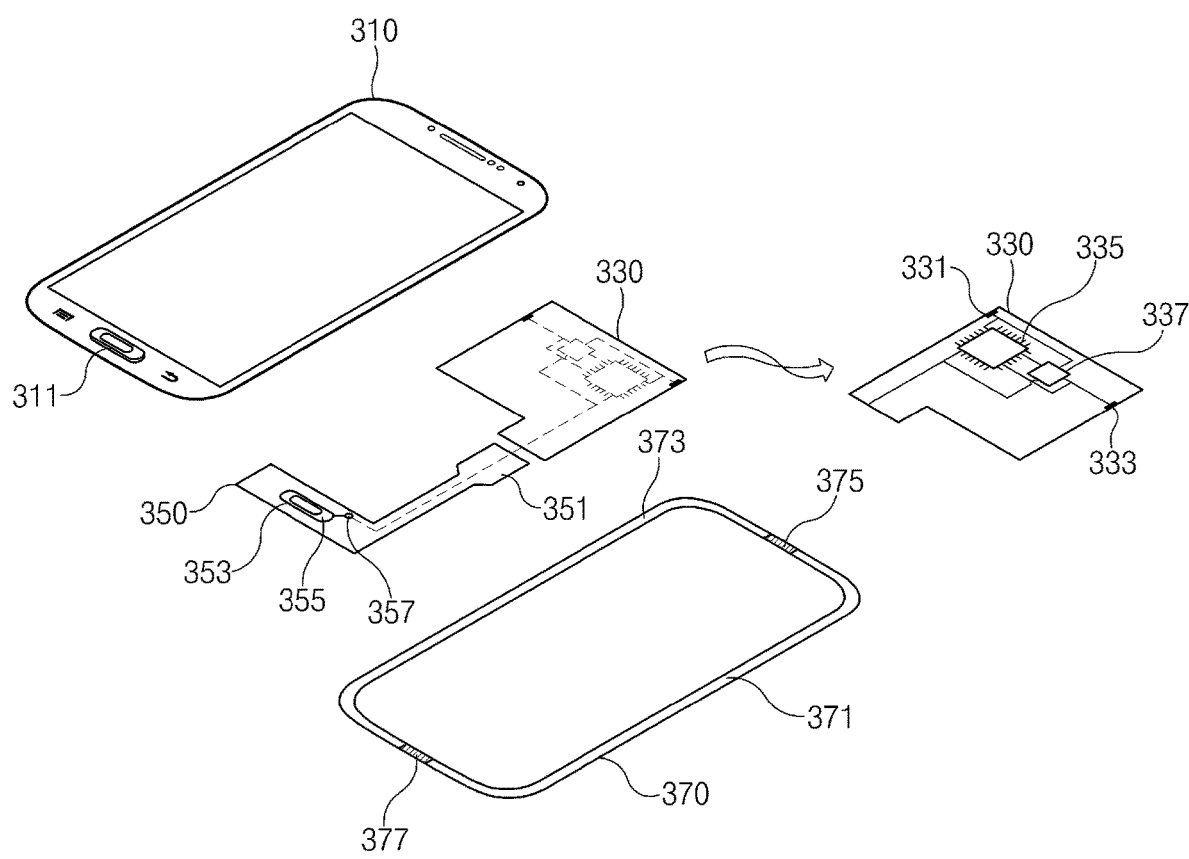
FIG. 3 illustrates an exploded perspective view of an example of an electronic device, according to various embodiments of the present disclosure.

FIG. 3 illustrates an exploded perspective view of an example of an electronic device, according to various embodiments of the present disclosure. Hereinafter, different features from the above-mentioned embodiments will be described in detail in order to avoid redundancy.

As illustrated in FIG. 3, an electronic device (e.g., the electronic device 101) according to various embodiments may include a physical button 311 (e.g., a home button) disposed on a front surface 310 thereof. One electrode may be disposed on the edge and/or surface of the physical button 211. According to another embodiment, the physical button 311 may include a plurality of electrodes disposed on the edge thereof and a plurality of insulators disposed between the electrodes such that the electrodes are not directly connected to each other.

According to various embodiments, the electronic device (e.g., the electronic device 101) may include a first printed circuit board 330 and a second printed circuit board 350. According to an embodiment, the first printed circuit board 330 and the second printed circuit board 350 may be integrated together. Additionally or alternatively, the first and second printed boards may be separate from another and connected via a printed circuit board connector 351.

The first printed circuit board 330 may include a first electrode connection portion 331 and a second electrode connection portion 333 and may be connected to a processor 335. In addition, the first printed circuit board 330 may further include a biometric information processing module 337. The first and second electrode connection portions 333 and 335 may connect first and second electrodes 371 and 373 to the first printed circuit board 330. The first and second electrodes 371 and 373 may be biometric electrodes disposed in areas (e.g., an edge) of a cover (e.g., a rear cover or a battery cover) of the electronic device. Although in the present example the biometric information module 337 is integrated into the first printed circuit board 330, in some implementations the biometric module 337 may be implemented on a separate printed circuit board that is connected to the first printed circuit board 330.

The processor 335 (e.g., the process 121) may analyze, store, or output the biometric information obtained through the electrodes (e.g., the first electrode 371 and the second electrode 373). According to an embodiment, the processor 335 may analyze the obtained biometric information on the basis of the user's biometric information stored in a memory included in the electronic device. For instance, the processor 335 may identify the user's health status by comparing biometric information stored in memory with biometric information obtained through the electrodes.

The biometric information processing module 337 (e.g., the biometric information processing module 123) may amplify or convert the biometric information. The biometric information processing module 337 may amplify or convert the biometric information obtained through the electrodes and supply the amplified or converted biometric information to the processor 335.

The second printed circuit board 350 may include a printed circuit board connector 351, a button connection area 353, a third electrode 355, and a hole 357. The button connection area 353 may electrically and/or physically connect the physical button 311 disposed at the front surface of the electronic device with the second printed circuit board 350. The third electrode 355 may be formed on the edge of the physical button 311. The physical button 311 may be disposed on the front surface of the electronic device. The hole 357 may serve as a connection path for a line connecting the third electrode 355 disposed on the second printed circuit board 350 and the processor 335 disposed on the first printed circuit board 330.

According to various embodiments, the electronic device (e.g., the electronic device 101) may include a cover 370 (e.g., a rear cover or a battery cover). The cover 370 may form one side surface of the housing or may be disposed inside the housing. For instance, when the cover 370 is a battery cover, the cover 370 may be removable from the housing. Additionally or alternatively, when the cover 370 is the rear cover, the cover 370 may be disposed inside the housing. According to various embodiments, the cover 370 may include a protruding edge for preventing the electronic device from slipping from the user's hand. According to an embodiment, the edge of the rear cover may protrude from a surface of the battery cover. In this case, the battery cover may include an opening formed therethrough such that the edge of the rear cover protrudes outside the surface of the battery cover. The cover 370 may include a first electrode 371, a second electrode 373, a first insulator 375, and a second insulator 377. As shown in FIG. 3, the first insulator 375 may be disposed in an upper-end area of the cover 370 and the second insulator 377 may be disposed in a lower end area of the cover 370. In addition, the first and second electrodes 371 and 373 may be separated from each other by the first and second insulators 375 and 377. In this case, the user may maintain contact with the first and second electrodes 371 and 373 while gripping the electronic device thereby permitting the electronic device to obtain biometric information via the third electrode 355.

According to various embodiments, the electrodes may be disposed in an area (e.g., the edge) of the one side surface of the housing to which the cover 370 is coupled instead of arranging the electrodes on the edge of the cover 370. For instance, the electrodes may be disposed on a conductor provided in the area (e.g., an area in which the side surface of the housing is connected to the rear surface of the housing), to or from which the battery cover is attached or detached, to support the battery cover and may be separated from each other with respect to an insulating material.

Figure 4:
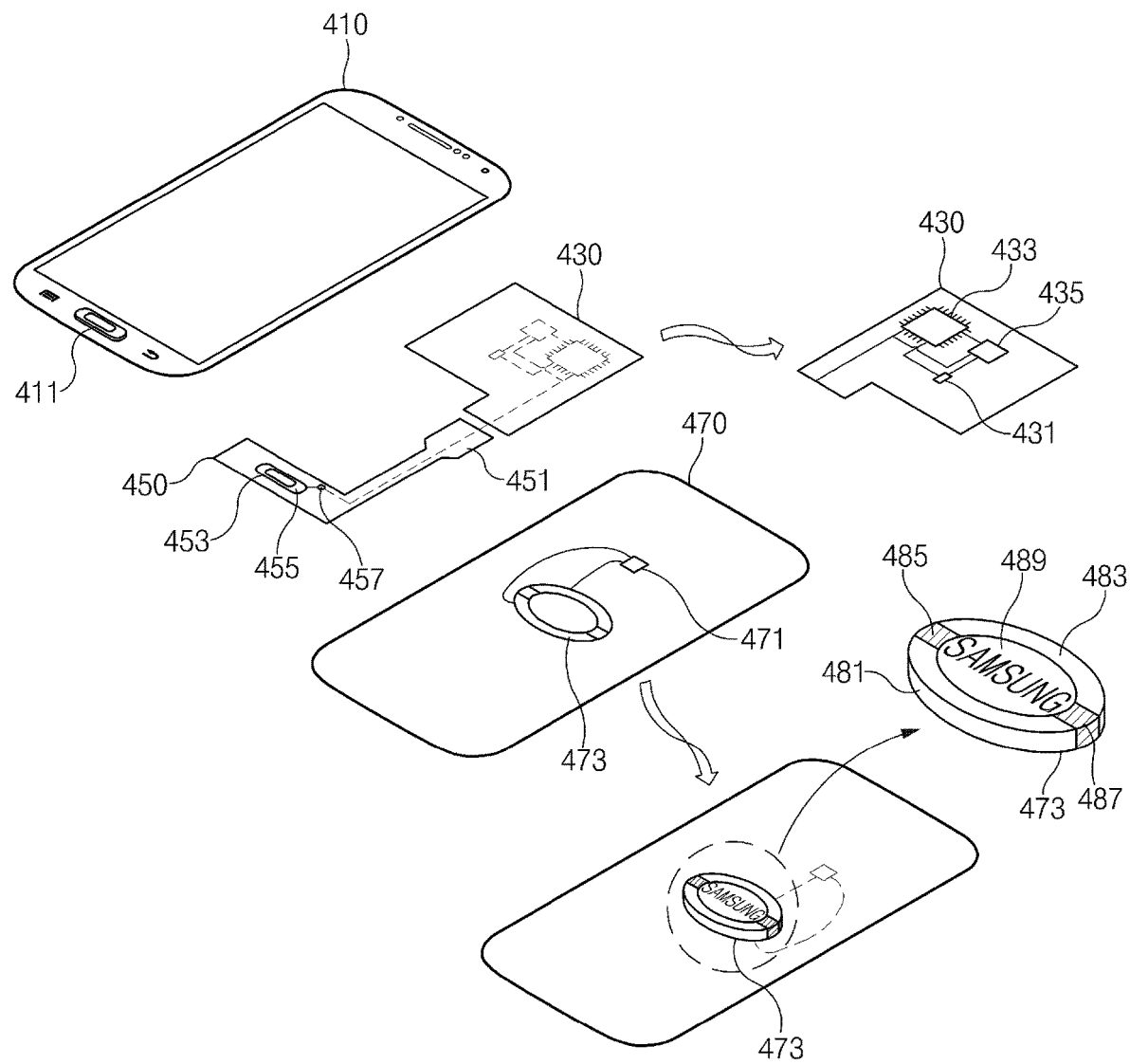
FIG. 4 illustrates an exploded perspective view of an example of an electronic device, according to various embodiments of the present disclosure.

FIG. 4 illustrates an exploded perspective view of an example of an electronic device, according to various embodiments of the present disclosure.

Referring to FIG. 4, an electronic device (e.g., the electronic device 101) according to various embodiments may include a physical button 411 (e.g., a home button) disposed on a front surface 410 thereof. One electrode may be disposed in the specific area of an edge or a surface of the physical button 411. Additionally or alternatively, in some implementations, the physical button 411 may include a plurality of electrodes disposed on the edge thereof and a plurality of insulators disposed between the electrodes such that the electrodes are not directly connected to each other.

According to various embodiments, the electronic device (e.g., the electronic device 101) may include a first printed circuit board 430 and a second printed circuit board 450. According to an embodiment, the first printed circuit board 430 and the second printed circuit board 450 may be integrated together. Additionally or alternatively, the first and second printed boards may be separate from another and connected via a printed circuit board connector 451.

The first printed circuit board 430 may include an electrode connection port 431 and may be connected to a processor 433. In addition, the first printed circuit board 430 may further include a biometric information processing module 435. The electrode connection port 431 may connect first and second electrodes 481 and 483 disposed on a logo badge 473 to the first printed circuit board 430. The first and second electrodes 481 and 483 may be biometric electrodes disposed in areas (e.g., an edge) of the logo badge 473 included in the battery cover 470. Although in the present example the biometric information module 435 is integrated into the first printed circuit board 430, in some implementations the biometric module 435 may be implemented on a separate printed circuit board connected to the printed circuit board 430.

The processor 433 (e.g., the processor 121) may analyze, store, or output the biometric information obtained through the electrodes (e.g., the first electrode 481 and the second electrode 483).

The biometric information processing module 435 (e.g., the biometric information processing module 123) may amplify or convert the biometric information. The biometric information processing module 435 may amplify or convert the biometric information obtained through the electrodes and supply the amplified or converted biometric information to the processor 433.

The second printed circuit board 450 may include a printed circuit board connector 451, a button connection area 453, a third electrode 455, and a hole 457. The button connection area 453 may electrically and/or physically connect the physical button 411 disposed at the front surface of the electronic device with the second printed circuit board 450. The third electrode 455 may be formed on the edge and/or the surface of the physical button 411. The hole 457 may serve as a connection path for a line connecting the third electrode 455 disposed on the second printed circuit board 450 with the processor 433 and/or the biometric information processing module 437, which is disposed on the first printed circuit board 430.

According to various embodiments, the electronic device (e.g., the electronic device 101) may include a battery cover 470. According to an embodiment, the battery cover 470 may include a logo badge 473 of a manufacturer or a service provider associated with the electronic device. According to aspects of the disclosure, the logo badge 473 may include the first electrode 481, the second electrode 483, a first insulator 485, and a second insulator 487, which are disposed in specific areas of an edge thereof. In addition, the logo badge 473 may include a material 489 disposed in the interior of the logo badge 473. The shaped material 489 may define the shape of the logo (e.g., the letters spelling "Samsung") represented by the logo badge 473.

According to various embodiments, the electrodes may be disposed in areas of the shaped material 489 instead of on the edge of the logo badge 473. For instance, the electrodes and the insulators may be disposed in areas of a character or an image corresponding to the shaped material 489. According to an embodiment, a plurality of characters or images, which correspond to the shaped material 489, may be formed of (or include) a conductive material, thereby permitting characters or images that are part of the logo to be used as electrodes. For instance, when the characters or images defined by the shaped material 489 are "Sb 5", the letter "S" and the number "5" may be used as a first electrode and a second electrode respectively. In some implementations, the first electrode may be disposed in the area of an edge or surface of the material having the shape of "S" and the second electrode may be disposed in the area of an edge or surface of the material having the shape of "5".

The electronic device may provide the biometric information obtained through the first electrode 481 or the second electrode 483 to at least one of the processor 433 or the biometric information processing module 435 through the electrode connection port 471. According to an embodiment, the electrode connection port 431 included in the first printed circuit board 430 may be connected to the electrode connection port 471 included in the battery cover 470. According to various embodiments, the logo badge 473 may be disposed on the rear cover of the electronic device. In such instances, the battery cover 470 may include an opening formed therethrough to allow the logo badge 473 to protrude through the battery cover 470.

The first structure (e.g., the biometric sensor 231) or the second structure (e.g., the physical button 211), which is shown in FIGS. 2 to 4, may be replaced with other structures included in the electronic device (e.g., the electronic device 101). For instance, the biometric sensor 231 may be replaced with a camera disposed on the rear surface of the electronic device 101. In this case, the electrodes may be formed on a deck of the camera. In addition, the physical button 211 may be replaced with a side button (e.g., a volume button) disposed on the side surface of the electronic device 101.

According to various embodiments, the first structure or the second structure may generate an input signal, e.g., a trigger signal, to indicate the start of measuring the biometric information. According to an embodiment, when the user performs a specific operation (e.g., an operation pushing the button during a predetermined time or more) on the second structure (e.g., the physical button 211) to perform a function included in the electronic device 101, the second structure may generate the trigger signal related to the measurement of the biometric information. For instance, with regard to the use of the biometric information measurement of a healthcare application previously installed in the electric device 101, the second structure may generate the trigger signal related to the biometric information measurement in response to the specific operation. According to various embodiments, the structures may generate the trigger signal through the electrodes disposed on the structures in response to the contact of the user's body.

According to various embodiments, the electronic device may include the first structure protruded outward from the surface of the housing of the electronic device and the electrodes disposed in the area of the first structure and spaced apart from each other by the insulating material.

According to various embodiments, the first structure may be disposed on the rear surface of the housing of the electronic device.

According to various embodiments, the first and second electrodes may be disposed in the areas of the first structure, the third electrode may be disposed in the area of the second structure disposed on the front surface or the side surface of the housing of the electronic device, the first electrode may be used as the ground electrode, and the second and third electrodes may be used as the measuring electrode.

According to various embodiments, the electronic device may be set to generate the input signal to indicate the start of measuring the biometric information when the portion of the user's body makes contact with the first, second, and third electrodes.

According to various embodiments, the first structure may be the biometric sensor, the first and second electrodes may be disposed in the areas of the edge of the biometric sensor, and the second structure may be the physical button.

According to various embodiments, the first structure may be the camera, the first and second electrodes may be disposed in the areas of the deck of the camera, and the second structure may be the physical button.

According to various embodiments, the first structure may be the logo, the first and second electrodes may be disposed in the areas of the edge of the logo or in the areas of the shaped material of the logo, and the second structure may be the physical button.

According to various embodiments, the first and second electrodes may be connected to at least one of the processor or the biometric information processing module of the electronic device through the electrode connection port disposed in the area adjacent to the logo.

According to various embodiments, the first structure may be the edge of the cover, the first and second electrodes may be disposed in the areas of the edge of the cover, the third electrode may be disposed in the area of the second structure disposed on the front or rear surface of the housing of the electronic device, the first electrode may be used as the ground electrode, and the second and third electrodes may be used as the measuring electrode.

According to various embodiments, the electronic device may be set to generate the input signal to indicate the start of measuring the biometric information when the portion of the user's body makes contact with at least one of the first electrode, the second electrode, or the third electrode.

Figure 5:
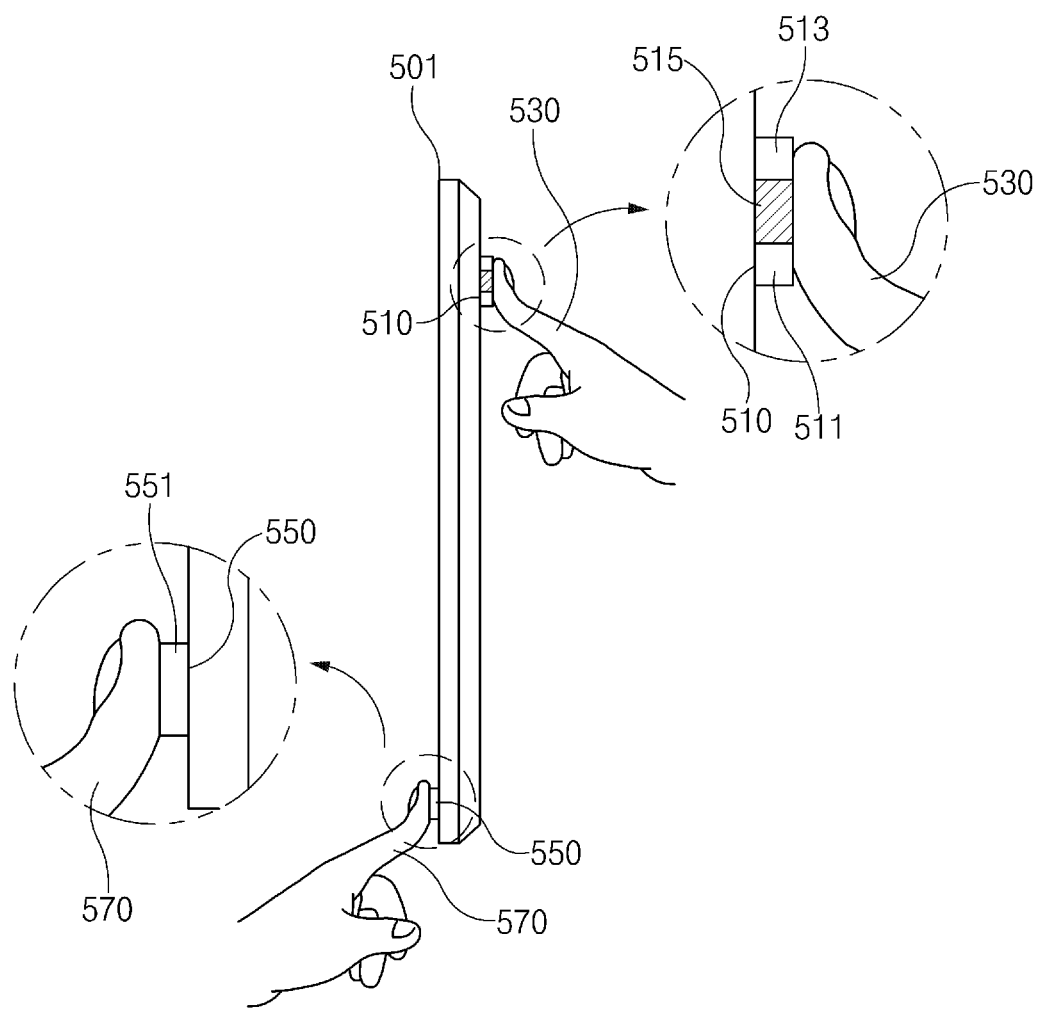
FIG. 5 is a diagram illustrating an example of the operation of an electronic device, according to various embodiments of the present disclosure.

FIG. 5 is a diagram illustrating an example of the operation of an electronic device, according to various embodiments of the present disclosure.

Referring to FIG. 5, an electronic device 501 according to various embodiments may include a first structure 510 or a second structure 550. The first structure 510 may include a first electrode 511, a second electrode 513, a first insulator 515, and a second insulator (not shown). For instance, the first and second electrodes 511 and 513 may be formed on the edge of the first structure 510 and may be separated from one another by the first insulator 515 and the second insulator (not shown). In addition, the second structure 550 may include a third electrode 551. For instance, the third electrode 551 may be disposed on the edge or surface of the second structure 550.

In this regard, the first electrode 511, the second electrode 513, or the third electrode 551, which are disposed on the first structure 510 and the second structure 550, may be used as the measuring electrode or the ground electrode related to the measuring operation of the biometric information. For instance, the electronic device 501 may use the second electrode 513 of two electrodes disposed on the first structure 510 as ground electrodes and may use the third electrode 551 disposed on the second structure 550 as a measuring electrode.

According to various embodiments, when a portion (e.g., a portion of a finger of the user's left-hand 570) of the user's body makes contact with the third electrode 551 while also making contact with the first and second electrodes 511 and 513, the electronic device 101 may begin measuring (e.g., collecting) biometric information of the user. Afterwards, the biometric information obtained through the electrodes may be amplified or converted by the biometric information processing module (e.g., the biometric information processing module 123), and then provided to the processor (e.g., the processor 121).

According to various embodiments, the second structure 550 may generate a signal that causes the electronic device to being measuring (e.g., collecting) the biometric information. For instance, when the portion of the user's body makes contact with the second structure 550 while the portion of the user's body makes contact with the first structure 510, the second structure 550 may generate the signal that triggers the measurement (e.g., collection) of the biometric information.

Figure 6:
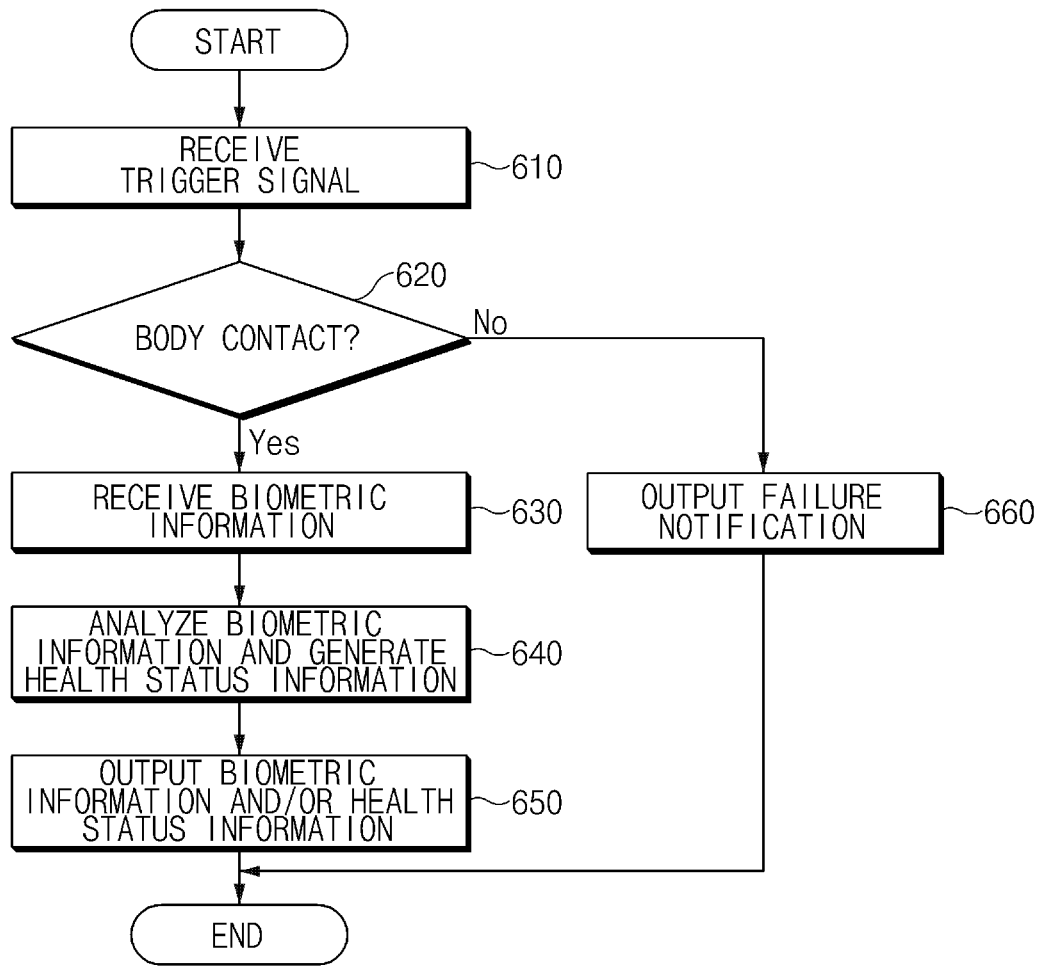
FIG. 6 is a flowchart of an example of a process, according to various embodiments of the present disclosure.

FIG. 6 is a flowchart of an example of a process, according to various embodiments of the present disclosure.

According to the process, in operation 610, the processor of an electronic device (e.g., the processor 121) may receive the trigger signal related to the measurement of the biometric information. The trigger signal may be received while an application (e.g., the healthcare application) included in the electronic device (e.g., the electronic device 101) is being executed. For example, the trigger signal may be generated in response to the user selecting a virtual button object displayed on a display of the electric device which corresponds to the biometric information measuring function of the healthcare application. As another example, the trigger signal may be generated when the user takes a specific action (e.g., an action shaking or overturning the electronic device at regular intervals or in a predetermined direction or an action making contact with or pressing the physical button, e.g., the home button or the side button, during a predetermined time or more). In addition, according to various embodiments, the trigger signal may be generated even when the healthcare application is not being executed. In such instances, the electronic device may execute (e.g., launch) the healthcare application in response to the generation of the trigger signal.

In operation 620, in response to the trigger signal, the processor may detect whether the user's body makes contact with the electrodes included in the electronic device. For instance, the processor may detect whether the user's body makes contact with the first and second electrodes 241 and 243 disposed in the first structure shown in FIG. 2 or the user's body makes contact with the third electrode 255 disposed in the second structure 211. In instances in which the electrodes include a touch sensor, the touch sensor may sense that a portion of the user's body has come in contact with the electrodes and output a trigger signal to the processor, in response.

When no contact between the user's body and the electrode is sensed (e.g., when at least one of the electrodes related to the biometric information measurement does not make contact with the user's body), the processor may output a failure notification with respect to the biometric information measuring operation as shown in operation 660. According to an embodiment, the processor may output a notification message that indicates that the electronic device has failed to collect biometric information. The notification message may be output on the display of the electronic device or through a voice output device, such as a speaker, included in the electronic device. In some implementations, the notification message may be presented on the display of the electronic device as a popup alert. According to various embodiments, the processor may output information notifying the failure of the measurement of the biometric information to at least one of external devices connected to the electronic device via a communications network.

According to aspects of the disclosure, when contact between the user's body and the electrodes is successfully established (e.g., when the portion of the user's body makes contact with each of the electrodes related to the biometric information measurement), the processor may obtain the biometric information through the electrodes as shown in operation 630. For instance, the processor may obtain the biometric information, e.g., the biometric resistance information, biometric electric potential information, etc., through the portion of the user's body making contact with the electrodes during. According to various embodiments, the processor may output an indication of the progress of the collection of the biometric information to at least one of an output device included in the electronic device or transmit the indication of the progress an external device connected to the electronic device via a communications network while the processor obtains the biometric information.

According to an embodiment, when the processor detects an event indicating that the contact between the user's body and the electrodes in the touch sensor has been lost while the biometric information is being collected, the processor may stop obtaining (e.g., collecting) the biometric information, and then analyze the collected biometric information. Additionally or alternatively, according to various embodiments, when the processor is configured to collect the biometric information during a predetermined time period, the processor may stop obtaining the biometric information at the end of this period. For instance, when the processor obtains the biometric information during a time set in the healthcare application or during a time set by the user, the processor may stop obtaining the biometric information, and then analyze the biometric information. According to various embodiments, when the processor is unable to obtain any biometric information during the predetermined time period, the processor may output a failure notification message indicating that the processor is unable to obtain the biometric information.

In operation 640, the processor may analyze (e.g. process) the obtained biometric information and generate health status information as a result. According to an embodiment, the biometric information obtained through the electrodes may be pre-processed, (e.g., amplified or converted to a particular format), by the biometric information processing module (e.g., the biometric information processing module 123) to generate pre-processed biometric information. The processor may then analyze at least some of the pre-processed biometric information. In some implementations, the processor may use the biometric information stored in the memory included in the electronic device. For instance, the processor may analyze the biometric information obtained during the predetermined time by using biometric information stored in the memory for a certain period of time. According to various embodiments, the processor may store at least one of the biometric information obtained through the electrodes, the biometric information processed by the biometric information processing module, or the biometric information analyzed by the processor in the memory together with the measuring time.

According to various embodiments, the processor may generate the health status information of the user as a result of analyzing the biometric information. In this case, the processor may use the health status information of the user, which are stored in the memory. According to an embodiment, the processor may generate the health status information of the user during the predetermined time by using the health status information corresponding to the certain period of time, which are stored in the memory. In addition, the processor may store the generated health status information of the user in the memory. According to various embodiments, the processor may store at least one of the biometric information or the health status information on one or more external devices that are connected to the electronic device via a communications network.

In operation 650, the processor may output the biometric information and/or the health status information of the user through the output device included in the electronic device. For instance, the processor may display an image, such as a graph, that identifies health status information obtained during the predetermined time. In addition, the processor may output the voice information corresponding to the health status information of the user through the voice output device on the basis of the analyzed biometric information. According to various embodiments, the processor may output information corresponding to at least one of the biometric information or the health status information to at least one of the external devices connected to the electronic device via a communications network.

According to various embodiments, the method of determining the health status of the user using the electronic device may include the operation of obtaining the biometric information of the user through the electrodes separately disposed in the areas of the first structure by the insulating material, which is protruded outward from the surface of the housing of the electronic device and the operation of determining the health status of the user on the basis of at least the biometric information.

According to various embodiments, the operation of obtaining the biometric information of the user may include the operation of obtaining the biometric information through the first and second electrodes disposed in the areas of the first structure and the third electrode disposed in the area of the second structure included in the electronic device.

According to various embodiments, the operation of obtaining the biometric information of the user may further include the operation of measuring the heart rate or the oxygen saturation level of the user through the biometric sensor when the first structure is the biometric sensor and the operation of measuring the electrocardiogram or the body fat ratio through the first, second, and third electrodes.

According to various embodiments, the operation of obtaining the biometric information of the user may further include the operation of obtaining the biometric information in response to the input signal generated when the portion of the user's body makes contact with the first, second, and third electrodes.

According to various embodiments, when at least one of the first electrode, the second electrode, or the third electrode does not make contact with the portion of the user's body, the operation of obtaining the biometric information of the user may further include the operation of outputting information notifying that it failed to obtain the biometric information to the output device included in the electronic device or at least one of the external devices connected to the electronic device via a communications network.

According to various embodiments, when the first electrode, the second electrode, and the third electrode make contact with the portion of the user's body, the operation of obtaining the biometric information of the user may further include the operation of outputting information notifying the obtained status of the biometric information to the output device included in the electronic device or at least one of the external devices connected to the electronic device via a communications network.

According to various embodiments, when the electrodes make contact with the portion of the user's body, the operation of determining the health status of the user may further include the operation of generating the health status information corresponding to the health status of the user, which is checked on the basis of the biometric information obtained while the electrodes are in contact with the portion of the user's body.

According to various embodiments, the operation of determining the health status of the user may further include the operation of storing at least one of the biometric information or the health status information in the memory included in the electronic device or at least one of the external devices connected to the electronic device via a communications network.

According to various embodiments, the operation of determining the health status of the user may further include the operation of outputting information corresponding to at least one the biometric information or the health status information to the output device included in the electronic device or at least one of the external devices connected to the electronic device via a communications network.

Figure 7:
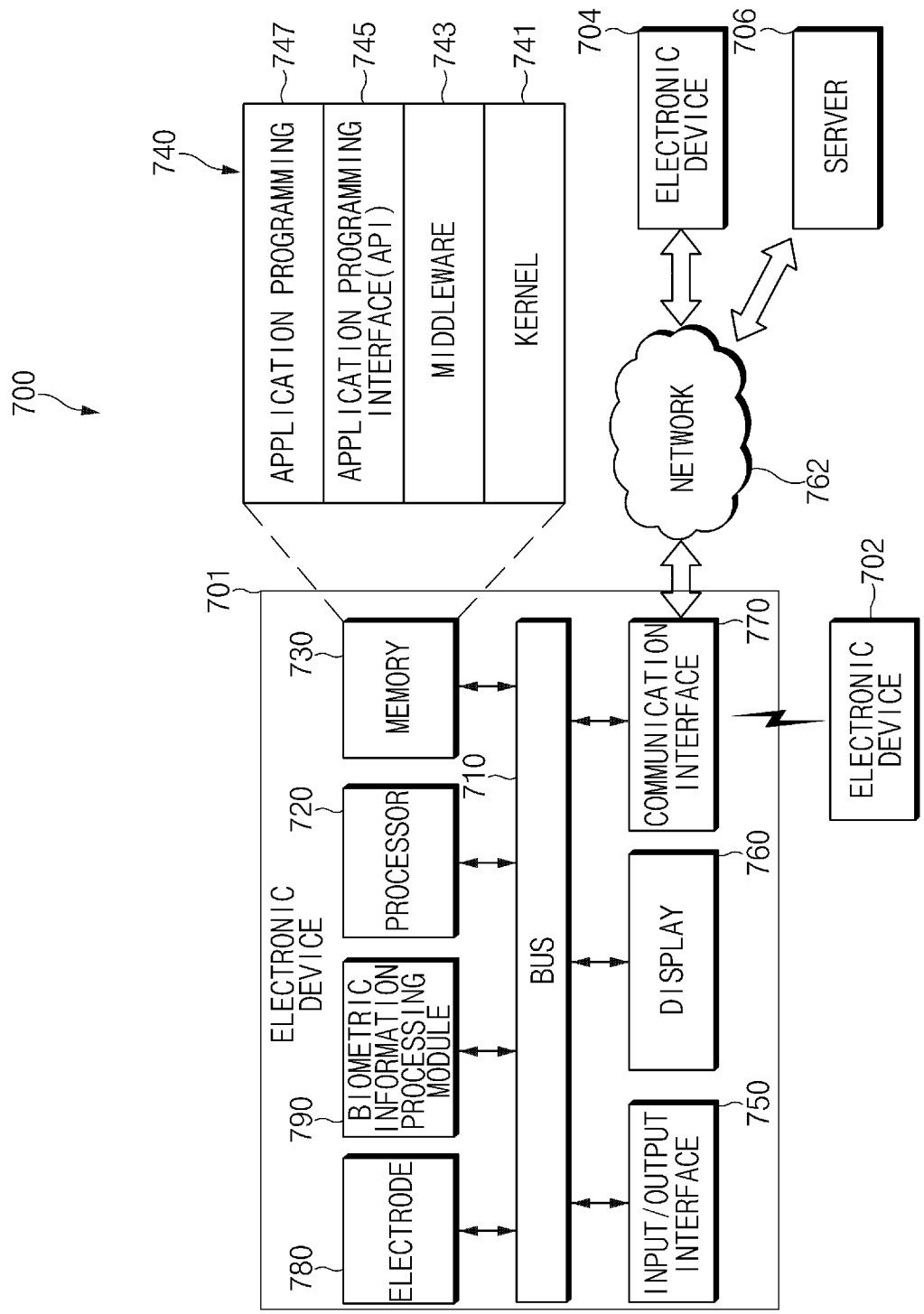
FIG. 7 is a block diagram of an example of an electronic device, according to various embodiments of the present disclosure.

FIG. 7 is a block diagram of an example of an electronic device, according to various embodiments of the present disclosure.

Referring to FIG. 7, there is illustrated an electronic device 701 in a network environment 700 according to various embodiments of the present disclosure. The electronic device 701 may include a bus 710, a processor 720, a memory 730, an input/output (I/O) interface 750, a display 760, a communication interface 770, one or more electrodes 780, and a biometric information processing module 790. According to an embodiment of the present disclosure, the electronic device 701 may not include at least one of the above-described components or may further include other component(s).

The bus 710 may interconnect the above-described components 710 to 790 and may be a circuit for conveying communications (e.g., a control message and/or data) among the above-described components.

The processor 720 may include any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), etc. The processor 720 may perform, for example, data processing or an operation associated with control or communication of at least one other component(s) of the electronic device 701.

According to various embodiments, the processor 720 (e.g., a processor 121) may execute operations or data processing associated with control and/communication of at least one component(s) associated with measuring of biometric information. For example, the processor 720 may analyze, store or output biometric information obtained through the electrode 780. Alternatively, the processor 720 may generate health status information of a user on the basis of the biometric information and store or output the generated health status information of the user.

The memory 730 may include any suitable type of volatile or non-volatile memory, such as Random-access Memory (RAM), Read-Only Memory (ROM), Network Accessible Storage (NAS), cloud storage, a Solid State Drive (SSD), etc. The memory 730 may store instructions or data associated with at least one other component(s) of the electronic device 701. According to various embodiments of the present disclosure, the memory 730 may store software and/or a program 740. The program 740 may include, for example, a kernel 741, a middleware 743, an application programming interface (API) 745, and/or an application (or an application program) 747. At least a portion of the kernel 741, the middleware 743, or the API 745 may be called an "operating system (OS)".

The kernel 741 may control or manage system resources (e.g., the bus 710, the processor 720, the memory 730, and the like) that are used to execute operations or functions of other programs (e.g., the middleware 743, the API 745, and the application program 747). Furthermore, the kernel 741 may provide an interface that allows the middleware 743, the API 745, or the application program 747 to access discrete components of the electronic device 701 so as to control or manage system resources.

The middleware 743 may perform a mediation role such that the API 745 or the application program 747 communicates with the kernel 741 to exchange data.

Furthermore, the middleware 743 may process task requests received from the application program 747 according to a priority. For example, the middleware 743 may assign the priority, which makes it possible to use a system resource (e.g., the bus 710, the processor 720, the memory 730, or the like) of the electronic device 701, to at least one of the application program 747. For example, the middleware 743 may process the one or more task requests according to their assigned priorities, which makes it possible to perform scheduling or load balancing on the one or more task requests.

The API 745 may be an interface through which the application program 747 controls a function provided by the kernel 741 or the middleware 743, and may include, for example, at least one interface or function (e.g., an instruction) for a file control, a window control, image processing, a character control, or the like.

According to various embodiments, the memory 730 may store at least one of biometric information obtained through the electrode 780, biometric information processed by the biometric information processing module 790, biometric information analyzed by the processor 720, or biometric information of the user generated by the processor 720. For example, the memory 730 may store the biometric information or health status information of the user together with an indication of the measurement time when the biometric information and/or health information was collected.

The I/O interface 750 may transmit an instruction or data, input from a user or another external device, to other component(s) of the electronic device 701. Furthermore, the I/O interface 750 may output an instruction or data, received from other component(s) of the electronic device 701 to a user or another external device.

According to various embodiments, the input/output interface 750 may output voice information, corresponding to health status information of the user analyzed through the processor 720, through a voice output device such as a speaker, an earphone, or the like.

The display 760 may include, for example, a liquid crystal display (LCD), a light-emitting diode (LED) display, an organic LED (OLED) display, or a microelectromechanical systems (MEMS) display, or an electronic paper display. The display 760 may display, for example, various contents (e.g., a text, an image, a video, an icon, a symbol, and the like) to a user. The display 760 may include a touch screen and may receive, for example, a touch, gesture, proximity, or hovering input using an electronic pen or a portion of a user's body.

According to various embodiments, the display 760 may display the biometric information or the health status information. For example, the display 760 may display an image object (e.g., a graph or the like) so as to correspond to health status information within a specific time.

The communication interface 770 may establish communication between the electronic device 701 and an external electronic device (e.g., a first external electronic device 702, a second external electronic device 704, or a server 706). For example, the communication interface 770 may be connected to a network 762 through wireless communication or wired communication to communicate with the external device (e.g., a second external electronic device 704 or a server 706).

Each of the first and second external electronic devices 702 and 704 may be a device of which the type is different from or the same as that of the electronic device 701. According to an embodiment of the present disclosure, the server 706 may include a group of one or more servers. According to various embodiments of the present disclosure, all or a part of operations that the electronic device 701 will perform may be executed by another or plural electronic devices (e.g., the electronic devices 702 and 704 and the server 706). According to an embodiment of the present disclosure, when the electronic device 701 executes any function or service automatically or in response to a request, the electronic device 701 may not perform the function or the service internally, but, alternatively additionally, it may request at least a portion of a function associated with the electronic device 701 at other device (e.g., the electronic device 702 or 704 or the server 706). The other electronic device (e.g., the electronic device 702 or 704 or the server 706) may execute the requested function or additional function and may transmit the execution result to the electronic device 701. The electronic device 701 may provide the requested function or service using the received result or may additionally process the received result to provide the requested function or service. To this end, for example, cloud computing, distributed computing, or client-server computing may be used.

The electrode 780 may obtain biometric information through contact with a portion of a user's body. According to various embodiments, the electrode 760 may be disposed on a structure included in the electronic device 701, such as a physical button (e.g., a home button), a biometric sensor, a cover, or a logo, or the like. According to various embodiments, electrodes included in structures spaced apart from each other by a predetermined distance may be utilized as the biometric electrode (e.g., the measuring electrode or the ground electrode). The biometric information obtained through the electrode 780 may be transmitted to at least one of the processor 720 and the biometric information processing module 790.

The biometric information processing module 790 may amplify and/or convert the biometric information to another format. Afterwards, the biometric information processing module 790 may supply the amplified or converted biometric information to the processor 720. The biometric information processing module 790 may amplify the biometric information provided through the electrodes, remove noise included in the biometric information, or convert the biometric information, and then may supply the biometric information to the processor 720. According to various embodiments, the function of the biometric information processing module 790 may be performed by the processor 720. Alternatively, the biometric information processing module 790 and the processor 720 may be separate electronic circuits that are integrated into one chip (e.g., system on chip (SoC)).

Figure 8:
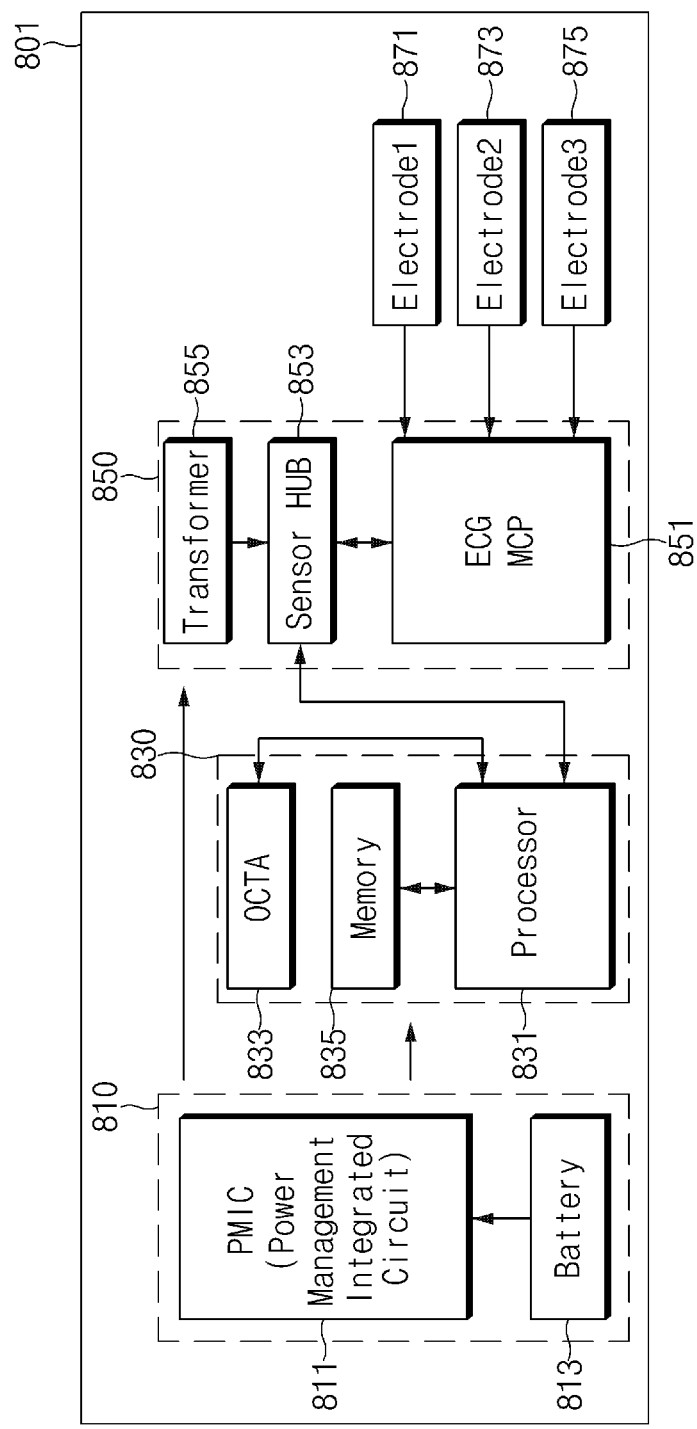
FIG. 8 is a block diagram of an example of an electronic device, according to various embodiments of the present disclosure.

FIG. 8 is a block diagram of an example of an electronic device 801, according to various embodiments of the present disclosure.

As illustrated, the electronic device 801 according to various embodiments may include a power supply part 810, a processing part 830, a signal input part 850, a first electrode 871, a second electrode 873, and a third electrode 875.

The power supply part 810 may supply power to the processing part 830 or the signal input part 850. The power supply part 810 may include a power management integrated circuit (PMIC) 811 or a battery 813. The PMIC 811 may serve as a module managing the use of the power source of the electronic device 801 and may be operated in a wire and/or wireless charging method. The battery 813 may include a rechargeable battery and/or a solar battery.

The processing part 830 may perform the function of calculating, storing, displaying, or processing information received from the signal input part 850. The processing part 830 may include a processor 831, an on-cell TSP amoled (OCTA) 833, or a memory 835. The processor 831 may execute calculation operation or data processing operation related to the control and/or communication of at least one other element of the electronic device 801. The processor 831 may include one or more of a central processing unit (CPU), an application processor (AP), or a communication processor (CP). According to various embodiments, the processor 831 may control a function of calculating, storing, displaying, or processing the biometric information received from the signal input part 850. The OCTA 833 may be a device obtained by mixing the display and the input device and may receive an input from the user and display information to the user. The OCTA 833 may display the biometric information or the health status information, which is processed by the processor 831. According to various embodiments, the OCTA 833 may be replaced with various input devices and display devices, which are included in the input/output interface 750 and the display 760 shown in FIG. 7. The memory 835 may perform a function of storing the biometric information or the health status information, which are processed by the processor 831.

The signal input part 850 may include an electrocardiogram multi-chip package (ECG MCP) 851, a sensor hub 853, or a transformer 855. The ECG MCP 851 may include circuits, components, or hardware devices, which can be used to generate a user's electrocardiogram. The ECG MCP 851 may perform to amplify or convert the biometric information (e.g., the biometric electric potential) received through the electrodes (e.g., the first electrode 871, the second electrode 873, or the third electrode 875). The sensor hub 853 may perform the function of gathering, processing or controlling information obtained from a plurality of sensors included in the electronic device 801. The transformer 855 may perform a function of insulating the processing part 830 from the signal input part 850. According to an embodiment, the transformer 855 may physically and separately connect the processing part 830 and the signal input part 850 using a transformer isolator to prevent signal interference from occurring when the biometric information (e.g., the biometric electric potential information) is being collected. For instance, the electrode including the ground electrode related to the biometric information measurement may be grounded on the basis of the transformer 855. According to various embodiments, all or a portion of the signal input part 850 may be included in the biometric information processing module 123 shown in FIG. 1A.

According to aspects of the disclosure, the electronic device 801 is configured to obtain a user's the electrocardiogram. According to various embodiment, the electronic device 802 may receive the biometric information of the user, e.g., the biometric electric potential information, through the electrodes, e.g., the first, second, and third electrodes 871, 873, and 875. The received biometric information may be amplified or converted by the ECG MCP 851. For example, the sensor hub 853 may perform a function of gathering, processing, or controlling the information of the ECG MCP 851 and the electrodes. The sensor hub 853 may supply the processed biometric electric potential information to the processor 831. The processor 831 may analyze the biometric electric potential information applied thereto using the biometric electric potential information stored in the memory 835 and generate the health status information associated with the user based on the analyzed biometric electric potential information. The processor 831 may store the biometric electric potential information applied thereto or the generated health status information in the memory 835 and display the biometric electric potential information applied thereto or the generated health status information through the OCTA 833.

Figure 9:
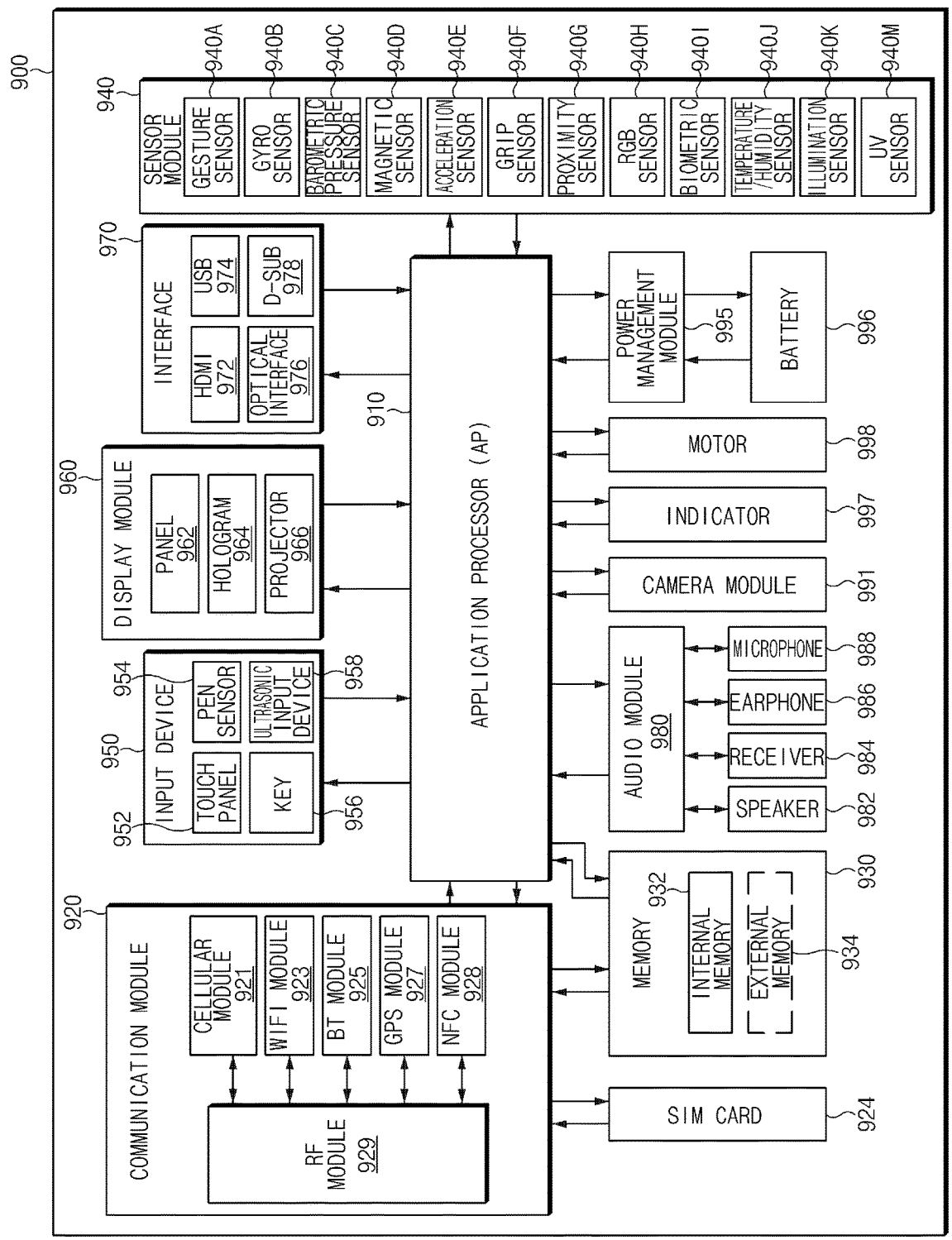
FIG. 9 is a block diagram of an example of an electronic device, according to various embodiments of the present disclosure.

FIG. 9 is a block diagram of an example of an electronic device 901, according to various embodiments of the present disclosure.

As illustrated, the electronic device 901 may include, for example, all or a part of an electronic device 701 illustrated in FIG. 7. The electronic device 901 may include one or more processors (e.g., an AP, a graphics processor, and the like) 910, a communication module 920, a subscriber identification module 924, a memory 930, a sensor module 940, an input device 950, a display module 960 (e.g., the display 160), an interface 970, an audio module 980, a camera module 991, a power management module 995, a battery 996, an indicator 997, and a motor 998.

The processor 910 may drive an operating system (OS) or an application to control a plurality of hardware or software components connected to the processor 910 and may process and compute a variety of data. The processor 910 may be implemented with a System on Chip (SoC), for example. According to an embodiment of the present disclosure, the processor 910 may further include a graphic processing unit (GPU) and/or an image signal processor. The processor 910 may include at least a part (e.g., a cellular module 921) of components illustrated in FIG. 9. The processor 910 may load and process an instruction or data, which is received from at least one of other components (e.g., a nonvolatile memory), and may store a variety of data in nonvolatile memory.

According to various embodiments, the processor 910 may execute operations or data processing associated with control and/or communication of at least one component(s) associated with measuring of biometric information. For example, the processor 910 may analyze, store or output biometric information obtained through electrodes (e.g., the first electrode 111 and the second electrode 113) illustrated in FIG. 1A and FIG. 1B. Alternatively, the processor 910 may generate health status information of a user on the basis of the biometric information and store or output the generated health status information of the user.

The communication module 920 may be configured the same as or similar to a communication interface 770 of FIG. 7. The communication module 920 may include a cellular module 921, a wireless-fidelity (Wi-Fi) module 923, a Bluetooth (BT) module 925, a global positioning system (GPS) module 927, a near field communication (NFC) module 928, and a radio frequency (RF) module 929.

The cellular module 921 may provide voice communication, video communication, a character service, an Internet service or the like through a communication network. According to an embodiment of the present disclosure, the cellular module 921 may perform discrimination and authentication of an electronic device 901 within a communication network using a subscriber identification module 924 (e.g., a SIM card), for example. According to an embodiment of the present disclosure, the cellular module 921 may perform at least a portion of functions that the processor 910 provides. According to an embodiment of the present disclosure, the cellular module 921 may include a communication processor (CP).

Each of the Wi-Fi module 923, the BT module 925, the GPS module 927, and the NFC module 928 may include a processor for processing data exchanged through a corresponding module, for example. According to an embodiment of the present disclosure, at least a portion (e.g., two or more components) of the cellular module 921, the Wi-Fi module 923, the BT module 925, the GPS module 927, and the NFC module 928 may be included within one Integrated Circuit (IC) or an IC package.

The RF module 929 may transmit and receive a communication signal (e.g., an RF signal). The RF module 929 may include a transceiver, a power amplifier module (PAM), a frequency filter, a low noise amplifier (LNA), an antenna, or the like. According to various embodiments of the present disclosure, at least one of the cellular module 921, the Wi-Fi module 923, the BT module 925, the GPS module 927, or the NFC module 928 may transmit and receive an RF signal by using a separate RF module.

The subscriber identification module 924 may include, for example, a subscriber identification module and may include unique identifying information (e.g., integrated circuit card identifier (ICCID)) or subscriber information (e.g., integrated mobile subscriber identity (IMSI)).

The memory 930 (e.g., a memory 1030) may include an internal memory 932 or an external memory 934. For example, the internal memory 932 may include at least one of a volatile memory (e.g., a dynamic random access memory (DRAM), a static RAM (SRAM), or a synchronous DRAM (SDRAM)), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a NAND flash memory, or a NOR flash memory), a hard drive, or a solid state drive (SSD).

The external memory 934 may include a flash drive, for example, compact flash (CF), secure digital (SD), micro secure digital (Micro-SD), mini secure digital (Mini-SD), extreme digital (xD), multimedia card (MMC), a memory stick, or the like. The external memory 934 may be functionally and/or physically connected to the electronic device 901 through various interfaces.

According to various embodiments, the memory 930 may store at least one of biometric information received through electrodes (e.g., the first electrode 111 or the second electrode 113) illustrated in FIG. 1A and FIG. 1B, biometric information processed through the biometric information processing module 123, biometric information analyzed by the processor 910, or biometric information of the user generated by the processor 910.

The sensor module 940 may measure, for example, a physical quantity or may detect an operation state of the electronic device 901. The sensor module 940 may convert the measured or detected information to an electric signal. The sensor module 940 may include at least one of a gesture sensor 940A, a gyro sensor 940B, a barometric pressure sensor 940C, a magnetic sensor 940D, an acceleration sensor 940E, a grip sensor 940F, a proximity sensor 940E a color sensor 940H (e.g., red, green, blue (RGB) sensor), a biometric sensor 940I, a temperature/humidity sensor 940J, an illuminance sensor 940K, or an UV sensor 940M. Although not illustrated, additionally or generally, the sensor module 940 may further include, for example, an E-nose sensor, an electromyography sensor (EMG) sensor, an electroencephalogram (EEG) sensor, an electrocardiogram (ECG) sensor, a photoplethysmographic (PPG) sensor, an infrared (IR) sensor, an iris sensor, and/or a fingerprint sensor. The sensor module 940 may further include a control circuit for controlling one or more sensors included therein. According to an embodiment of the present disclosure, the electronic device 901 may further include a processor which is a part of the processor 910 or independent of the processor 910 and is configured to control the sensor module 940. The processor may control the sensor module 940 while the processor 910 remains in a sleep state.

According to various embodiments, the sensor module 940 may include all or a part of the signal input part 850 illustrated in FIG. 8. According to an embodiment, the sensor module 940 may amplify or convert biometric information, received through a plurality of electrodes, that is, biometric potential information based on the ECG sensors included in the sensor module 940 and may transmit the amplified or converted result to the processor 910.

The input device 950 may include, for example, a touch panel 952, a (digital) pen sensor 954, a key 956, or an ultrasonic input device 958. The touch panel 952 may use at least one of capacitive, resistive, infrared and ultrasonic detecting methods. Also, the touch panel 952 may further include a control circuit. The touch panel 952 may further include a tactile layer to provide a tactile reaction to a user.

The (digital) pen sensor 954 may be, for example, a part of a touch panel or may include an additional sheet for recognition. The key 956 may include, for example, a physical button, an optical key, a keypad, and the like. The ultrasonic input device 958 may detect (or sense) an ultrasonic signal, which is generated from an input device, through a microphone (e.g., a microphone 988) and may check data corresponding to the detected ultrasonic signal.

The display module 960 (e.g., a display 1060) may include a panel 962, a hologram device 964, or a projector 966. The panel 962 may be configured the same as or similar to a display 760 of FIG. 7. The panel 962 and the touch panel 952 may be integrated into a single module. The hologram device 964 may display a stereoscopic image in a space using a light interference phenomenon. The projector 966 may project light onto a screen so as to display an image. The screen may be arranged on the inside or the outside of the electronic device 901. According to an embodiment of the present disclosure, the display module 960 may further include a control circuit for controlling the panel 962, the hologram device 964, or the projector 966.

According to various embodiments, the display module 960 may store at least one of biometric information obtained through electrodes (e.g., the first electrode 111 or the second electrode 113) illustrated in FIG. 1A and FIG. 1B, biometric information processed through the biometric information processing module 123, biometric information analyzed by the processor 910, or biometric information of the user generated by the processor 910.

The interface 970 may include, for example, an HDMI (high-definition multimedia interface) 972, a USB (universal serial bus) 974, an optical interface 976, or a D-sub (D-sub-miniature) 978. The interface 970 may be included, for example, in a communication interface 770 illustrated in FIG. 7. Additionally or alternatively, the interface 970 may include, for example, a mobile high definition link (MHL) interface, an SD card/multi-media card (MMC) interface, or an infrared data association (IrDA) standard interface.

The audio module 980 may convert a sound and an electric signal in dual directions. At least a portion of the audio module 980 may be included, for example, in an input/output interface 750 illustrated in FIG. 7. The audio module 980 may process, for example, sound information that is input or output through a speaker 982, a receiver 984, an earphone 986, or a microphone 988.

The camera module 991 for photographing a still image or a video may include, for example, at least one image sensor (e.g., a front sensor or a rear sensor), a lens, an image signal processor (ISP), or a flash (e.g., an LED or a xenon lamp).

The power management module 995 may manage, for example, the power supply of the electronic device 901. According to an embodiment of the present disclosure, a power management integrated circuit (PMIC) a charger IC, or a battery or fuel gauge may be included in the power management module 995. The PMIC may have a wired charging method and/or a wireless charging method. The wireless charging method may include, for example, a magnetic resonance method, a magnetic induction method or an electromagnetic method and may further include an additional circuit, for example, a coil loop, a resonant circuit, or a rectifier, and the like. The battery gauge may measure, for example, a remaining capacity of the battery 996 and a voltage, current or temperature thereof while the battery is charged. The battery 996 may include, for example, a rechargeable battery or a solar battery.

The indicator 997 may display a specific state of the electronic device 901 or a portion thereof (e.g., a processor 910), such as a booting state, a message state, a charging state, and the like. The motor 998 may convert an electrical signal into a mechanical vibration and may generate the following effects: vibration, haptic, and the like. Although not illustrated, a processing device (e.g., a GPU) for supporting a mobile TV may be included in the electronic device 901. The processing device for supporting a mobile TV may process media data according to the standards of DMB, digital video broadcasting (DVB), MediaFlo™, or the like.

Each of the above-mentioned elements of the electronic device according to various embodiments of the present disclosure may be configured with one or more components, and the names of the elements may be changed according to the type of the electronic device. The electronic device according to various embodiments of the present disclosure may include at least one of the above-mentioned elements, and some elements may be omitted or other additional elements may be added. Furthermore, some of the elements of the electronic device according to various embodiments of the present disclosure may be combined with each other so as to form one entity, so that the functions of the elements may be performed in the same manner as before the combination.

Figure 10:
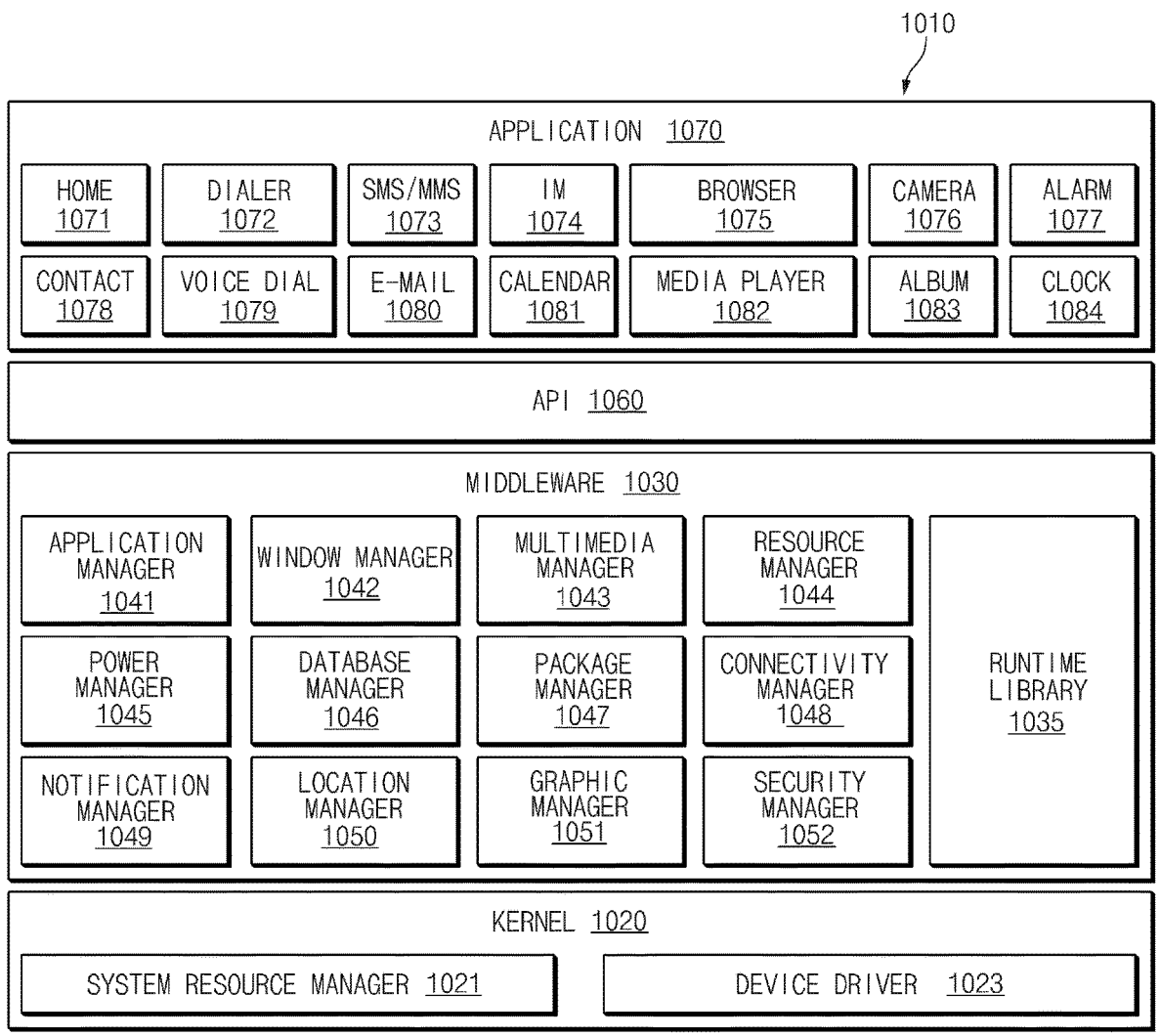
FIG. 10 is a block diagram of an example of a program module, according to various embodiments of the present disclosure.

FIG. 10 illustrates a block diagram of a program module 1010 according to various embodiments of the present disclosure.

Referring to FIG. 10, according to an embodiment of the present disclosure, a program module 1010 (e.g., a program 740) may include an operating system (OS) to control resources associated with an electronic device (e.g., an electronic device 701), and/or diverse applications (e.g., an application program 747) driven on the OS. The OS may be, for example, android, iOS, windows, symbian, tizen, or bada.

The program module 1010 may include a kernel 1020, a middleware 1030, an application programming interface (API) 1060, and/or an application 1070. At least a part of the program module 1010 may be preloaded on an electronic device or may be downloadable from an external electronic device (e.g., an electronic device 702 or 704, a server 706, and the like).

The kernel 1020 (e.g., a kernel 741) may include, for example, a system resource manager 1021 or a device driver 1023. The system resource manager 1021 may perform control, allocation, or retrieval of system resources. According to an embodiment of the present disclosure, the system resource manager 1021 may include a process managing part, a memory managing part, or a file system managing part. The device driver 1023 may include, for example, a display driver, a camera driver, a Bluetooth driver, a common memory driver, a USB driver, a keypad driver, a Wi-Fi driver, an audio driver, or an inter-process communication (IPC) driver.

The middleware 1030 may provide, for example, a function which the application 1070 needs in common, or may provide diverse functions to the application 1070 through the API 1060 to allow the application 1070 to efficiently use limited system resources of the electronic device. According to an embodiment of the present disclosure, the middleware 1030 (e.g., a middleware 743) may include at least one of a runtime library 1035, an application manager 1041, a window manager 1042, a multimedia manager 1043, a resource manager 1044, a power manager 1045, a database manager 1046, a package manager 1047, a connectivity manager 1048, a notification manager 1049, a location manager 1050, a graphic manager 1051, or a security manager 1052.

The runtime library 1035 may include, for example, a library module which is used by a compiler to add a new function through a programming language while the application 1070 is being executed. The runtime library 1035 may perform input/output management, memory management, or capacities about arithmetic functions.

The application manager 1041 may manage, for example, a life cycle of at least one application of the application 1070. The window manager 1042 may manage a GUI resource which is used in a screen. The multimedia manager 1043 may identify a format necessary for playing diverse media files, and may perform encoding or decoding of media files by using a codec suitable for the format. The resource manager 1044 may manage resources such as a storage space, memory, or source code of at least one application of the application 1070.

The power manager 1045 may operate, for example, with a basic input/output system (BIOS) to manage a battery or power, and may provide power information for an operation of an electronic device. The database manager 1046 may generate, search for, or modify database which is to be used in at least one application of the application 1070. The package manager 1047 may install or update an application which is distributed in the form of a package file.

The connectivity manager 1048 may manage, for example, wireless connection such as Wi-Fi or Bluetooth. The notification manager 1049 may display or notify an event such as arrival message, promise, or proximity notification in a mode that does not disturb a user. The location manager 1050 may manage location information of an electronic device. The graphic manager 1051 may manage a graphic effect that is provided to a user, or manage a user interface relevant thereto. The security manager 1052 may provide a general security function necessary for system security or user authentication. According to an embodiment of the present disclosure, when an electronic device (e.g., an electronic device 701) includes a telephony function, the middleware 1030 may further include a telephony manager for managing a voice or video call function of the electronic device.

The middleware 1030 may include a middleware module that combines diverse functions of the above-described components. The middleware 1030 may provide a module specialized to each OS kind to provide differentiated functions. Additionally, the middleware 1030 may remove a part of the preexisting components, dynamically, or may add a new component thereto.

The API 1060 (e.g., an API 745) may be, for example, a set of programming functions and may be provided with a configuration which is variable depending on an OS. For example, when the OS is Android, it may be permissible to provide one API set per platform. When the OS is Tizen, it may be permissible to provide two or more API sets per platform.

The application 1070 (e.g., an application program 747) may include, for example, one or more applications capable of providing functions for a home 1071, a dialer 1072, an SMS/MMS 1073, an instant message (IM) 1074, a browser 1075, a camera 1076, an alarm 1077, a contact 1078, a voice dial 1079, an e-mail 1080, a calendar 1081, a media player 1082, am album 1083, and a clock 1084, or for offering health care (e.g., measuring an exercise quantity or blood sugar) or environment information (e.g., atmospheric pressure, humidity, or temperature).

According to an embodiment of the present disclosure, the application 1070 may include an application (hereinafter referred to as "information exchanging application" for descriptive convenience) to support information exchange between the electronic device (e.g., an electronic device 701) and an external electronic device (e.g., an electronic device 702 or 704). The information exchanging application may include, for example, a notification relay application for transmitting specific information to the external electronic device, or a device management application for managing the external electronic device.

For example, the information exchanging application may include a function of transmitting notification information, which arise from other applications (e.g., applications for SMS/MMS, e-mail, health care, or environmental information), to an external electronic device (e.g., an electronic device 702 or 704). Additionally, the information exchanging application may receive, for example, notification information from an external electronic device and provide the notification information to a user.

The device management application may manage (e.g., install, delete, or update), for example, at least one function (e.g., turn-on/turn-off of an external electronic device itself (or a part of components) or adjustment of brightness (or resolution) of a display) of the external electronic device (e.g., an electronic device 702 or 704) which communicates with the electronic device, an application running in the external electronic device, or a service (e.g., a call service or a message service) provided from the external electronic device.

According to an embodiment of the present disclosure, the application 1070 may include an application (e.g., a health care application) which is assigned in accordance with an attribute (e.g., an attribute of a mobile medical device as a kind of electronic device) of the external electronic device (e.g., an electronic device 702 or 704). According to an embodiment of the present disclosure, the application 1070 may include an application which is received from an external electronic device (e.g., a server 106 or an electronic device 702 or 704). According to an embodiment of the present disclosure, the application 1070 may include a preloaded application or a third party application which is downloadable from a server. The component titles of the program module 1010 according to the embodiment of the present disclosure may be modifiable depending on kinds of OSs.

According to various embodiments of the present disclosure, at least a portion of the program module 1010 may be implemented by software, firmware, hardware, or a combination of two or more thereof. At least a portion of the program module 1010 may be implemented (e.g., executed), for example, by a processor (e.g., a processor 910). At least a portion of the program module 1010 may include, for example, modules, programs, routines, sets of instructions, or processes, or the like for performing one or more functions.

According to the above, since the electrode is disposed in the predetermined area of the structure included in the electronic device, a space utilization may be improved.

In addition, since the electrode is disposed in the predetermined area of the structure included in the electronic device, visual appearance issues of the electronic device may be solved.

FIGS. 1-10 are provided as an example only. At least some of the operations discussed with respect to these figures can be performed concurrently, performed in different order, and/or altogether omitted. It will be understood that the provision of the examples described herein, as well as clauses phrased as "such as," "e.g.", "including", "in some aspects," "in some implementations," and the like should not be interpreted as limiting the claimed subject matter to the specific examples.

The above-described aspects of the present disclosure can be implemented in hardware, firmware or via the execution of software or computer code that can be stored in a recording medium such as a CD-ROM, a Digital Versatile Disc (DVD), a magnetic tape, a RAM, a floppy disk, a hard disk, or a magneto-optical disk or computer code downloaded over a network originally stored on a remote recording medium or a non-transitory machine-readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. Any of the functions and steps provided in the Figures may be implemented in hardware, software or a combination of both and may be performed in whole or in part within the programmed instructions of a computer. No claim element herein is to be construed under the provisions of 35 U.S.C. 112, sixth paragraph, unless the element is expressly recited using the phrase "means for".

While the present disclosure has been particularly shown and described with reference to the examples provided therein, it will be understood by those skilled in the art that various changes in form and details may be made therein without departing from the spirit and scope of the present disclosure as defined by the appended claims.

What is claimed is:

1. An electronic device comprising:
a display;
a housing including a front housing through which the display is exposed, and a rear cover forming a rear surface of the electronic device opposite the front housing, wherein the rear cover defines an opening;
at least one processor, operably coupled to a plurality of first electrodes and photoplethysmographic (PPG) sensor via a printed circuit board that is at least partially enclosed between the front housing and the rear cover;
a first structure protruding through the opening as to extend outwardly from the rear surface of the housing; and
the plurality of first electrodes electrically coupled to the printed circuit board through the opening of the rear cover,
wherein:
the plurality of electrodes are disposed on a first surface of the first structure along an edge of the first surface,
the plurality of electrodes are electrically separated from one another by at least two insulators disposed along the edge of the first surface,
the plurality of electrodes and the at least two insulators as disposed on the edge occupy a circumference of the first structure, and
the PPG sensor is disposed on the first surface of the first structure such that the plurality of electrodes and the at least two insulators circumferentially surround an entirety of the PPG sensor.

2. The electronic device of claim 1, wherein the first structure is disposed on the rear surface of the electronic device.

3. The electronic device of claim 2, further comprising a second electrode disposed on a second structure that is arranged on a front surface or a side surface of the housing, wherein one of the first electrodes includes a ground electrode, and another one of the first electrodes includes a measuring electrode.

4. The electronic device of claim 3, further comprising a memory operatively coupled to the at least one processor, wherein the at least one processor is configured to start measuring biometric information when a portion of a user's body makes contact with the plurality of first electrodes and the second electrode.

5. The electronic device of claim 3, wherein:
the first structure includes a biometric sensor, the first electrodes are disposed adjacently to an edge of the biometric sensor, and the second structure includes a physical button.

6. The electronic device of claim 3, wherein the first structure includes a camera, and the second structure includes a physical button.

7. The electronic device of claim 3, wherein:
the first structure includes a logo badge,
the plurality of first electrodes include a first and a second electrode which are disposed adjacently to an edge of the logo badge or in a portion of the logo badge that defines a shape of the logo badge, and
the second structure includes a physical button.

8. The electronic device of claim 7, further comprising a memory operatively coupled to the at least one processor, wherein the first electrodes are coupled to the at least one processor via an electrode connection port disposed adjacently to the logo badge.

9. The electronic device of claim 1, further comprising a second electrode disposed on a second structure located on at least one of a front surface or the rear surface of the electronic device, wherein: the first structure includes an edge of a cover, the plurality of first electrodes includes a measuring electrode and a ground electrode, and the second electrode includes a measuring electrode.

10. The electronic device of claim 9, further comprising a memory operatively coupled to the at least one processor, wherein the at least one processor is configured to start measuring when a portion of a user's body makes contact with the plurality of first electrodes and the second electrode.

11. The electronic device of claim 1, wherein the plurality of first electrodes disposed on the first structure includes a first electrode and a second electrode, the electronic device further comprising:
a second structure extending outwardly from the front housing, the second structure including a third electrode.

12. The electronic device of claim 11, further comprising:
memory storing programming instructions executable by the at least one processor to cause the electronic device to:
when touch inputs are detected to the first and second structures, detect biometric information through the touch inputs by operating the first electrode and the second electrode as ground electrodes, and the third electrode as a measuring electrode.

* * * * *